United States Patent

Tsuyuki et al.

[11] Patent Number: 5,547,457
[45] Date of Patent: Aug. 20, 1996

[54] OBJECTIVE OPTICAL SYSTEM FOR ENDOSCOPES

[75] Inventors: Hiroshi Tsuyuki; Akira Kikuchi, both of Tokyo-to, Japan

[73] Assignee: Olympus Optical Co., Ltd., Tokyo-to, Japan

[21] Appl. No.: 184,062

[22] Filed: Jan. 21, 1994

[30] Foreign Application Priority Data

Jan. 22, 1993 [JP] Japan .................................. 5-025968

[51] Int. Cl.⁶ ...................................................... A61B 1/06
[52] U.S. Cl. ........................... 600/175; 600/176; 600/173; 600/160; 359/239
[58] Field of Search ..................... 600/127, 129, 600/160, 175, 176, 167, 168, 173, 174; 359/462, 466, 480, 239; 385/115, 116, 117, 902

[56] References Cited

U.S. PATENT DOCUMENTS

| | | | |
|---|---|---|---|
| 4,273,109 | 6/1981 | Enderby | 600/175 |
| 4,558,691 | 12/1985 | Okada | 600/175 X |
| 4,660,982 | 4/1987 | Okada | 600/175 X |
| 4,706,653 | 11/1987 | Yamamoto | 600/175 |
| 4,747,661 | 5/1988 | Ohkilwa | 350/96.26 |
| 4,765,313 | 8/1988 | Kumakura | 600/175 X |
| 4,787,370 | 11/1988 | Kanamori | 600/175 |
| 4,856,495 | 8/1989 | Tohjoh et al. | 600/175 |
| 4,941,457 | 7/1990 | Hasegawa | 600/175 X |

FOREIGN PATENT DOCUMENTS 63-291019  11/1988  Japan .
63-298314  12/1988  Japan .

Primary Examiner—Richard J. Apley
Assistant Examiner—Beverly M. Flanagan
Attorney, Agent, or Firm—Cushman, Darby & Cushman

[57] ABSTRACT

An objective optical system for endoscopes comprising a plurality of lens components and an aperture stop, and configured so as to permit adjusting a distance to an object to be observed simply by exchanging a lens component disposed in the vicinity of the aperture stop with another lens component having a focal length different from that of the lens component disposed in the vicinity of the aperture stop. This objective optical system for endoscopes can have an optimum depth of field by changing a diameter of the aperture stop along with the exchange of the lens component disposed in the vicinity of the aperture stop.

6 Claims, 23 Drawing Sheets

5,547,457

OBJECTIVE OPTICAL SYSTEM FOR ENDOSCOPES

BACKGROUND OF THE INVENTION

1. Field of the Invention

The present invention relates to an objective optical system for endoscopes, and more specifically to an objective optical system for endoscopes which comprises a plurality of lens components including one comprising an aperture stop and is configured so as to permit adjusting a distance to an object to be observed by disposing one of optical members having focal lengths different from one another selectively in the vicinity of the aperture stop comprised in the lens component.

2. Description of the Prior Art

In the recent years, there are widely used medical endoscopes which permit observing organs in human bodies with slender portions inserted into human body cavities and elaborately diagnosing abnormal locations by sampling biological tissues with forceps inserted through forceps channels as occasion demands. Further, in industrial fields also, industrial endoscopes are widely used for observing and inspecting interiors of boilers, turbines, engines, chemical plants and so on.

In case of the industrial endoscopes, in particular, a direct viewing type adaptor is used when an object to be observed is located in front of a leading end of the slender inserting portion in a longitudinal direction thereof or a side viewing type adaptor is selected when an inside wall surface or an object to be observed is located in a direction perpendicular to the inserting direction of the inserting portion. For such observation purposes, it is often practised to select an adaptor which has a field angle optimum for the location of the object to be observed simultaneously with the adaptor described above.

Since endoscopes are relatively expensive, it is very effective, from an economical viewpoint, to provide a leading end adaptor type of endoscope which can be equipped with a leading end adaptor having a viewing direction and a field angle optimum for a location of an object to be observed. Though the endoscope which is equipped with such a leading end adaptor permits observing an object in an optimum viewing direction and at an optimum field angle, the endoscope requires any focusing means for observing objects in a variety of observing conditions.

In order to solve the problem described above, the optical system for endoscopes disclosed by Japanese Patent Kokai Publication No. Sho 63-291,019 adopts an objective lens system using a means which moves, along an optical axis, certain lens components disposed in the objective lens system for focusing the optical system on an object to be observed through endoscopes. However, such a focusing means disposed in the optical system to be built in a main body of an endoscope makes it difficult to configure endoscopes compact and is therefore undesirable for use in an optical system for endoscopes which are to be configured compact.

Further, there are known objective optical systems for endoscopes which perform focusing by driving objective lens systems with piezoelectric actuators using piezoelectric elements as well as objective optical systems for endoscopes which permit remote control of objective lens systems with manual controllers utilizing force transmitting means such as wires.

When optical systems for endoscopes are to be focused by moving objective lens systems, however, the optical systems are apt to require tedious operations for focusing. When a wire is used as a force transmitting means, for example, the wire is built in an inserting portion and is moved by operating a mechanism for bending a distal end or bending the inserting portion, thereby making it difficult to keep an optical system for endoscopes in an optimum focused condition and inevitably degrading operability of the endoscope which uses the optical system. Further, the optical system which uses the optical system comprising the wire requires forcusing operations to be repeated each time the endoscope is to be set for observing another object, thereby complicating operations of the endoscope for observations. When the piezoelectric actuator is used in place of the wire for moving an objective lens system, it is difficult to configure a controller for the piezoelectric actuator and the piezoelectric actuator is also undesirable for use in endoscopes which should be configured as compactly as possible.

Furthermore, there is known a leading end adaptor type endoscope, as exemplified by the one disclosed by Japanese Patent Kokai Publication No. Sho 63-298,314, which is configured so as to perform focusing by using a focusing mechanism disposed in a leading end adaptor to be attached to a front lens component built in an objective lens system.

FIG. 2 shows a sectional view illustrating the leading end of the endoscope and the leading end adaptor. As is seen from this drawing, the leading end of the endoscope has a main body M which comprises an observation optical system which consists of an objective lens system O and an image guide fiber bundle IG as well as an illumination light guide fiber bundle LG disposed in parallel with the observation optical system. Further, disposed in the main body M is a wire passage through which a wire WM having an engaging end E extends to a manual controller. Attached to the other end of the wire WM is a rack R which engages with a pinion PI fixed to a control knob arranged on the manual controller.

On the other hand, a light guide fiber bundle LG, an observation optical system which comprises a negative lens component $L_1$, another lens component $L_F$ attached to a movable frame and a cover glass plate CG are disposed in parallel with each other in the adaptor AD. Attached to the movable frame is the wire WM having the engaging portion E at one end thereof. Further, a tapped ring is rotatably fitted over the adaptor AD.

The main body M of the endoscope is coupled with the adaptor in such a manner that optical axes of the illumination light guide fiber bundles LG disposed therein are aligned with each other and optical axes of sections of the illumination optical systems disposed therein are also aligned with each other, and the adaptor is attached to the main body M of the endoscope by screwing the tapped ring over thread formed on the main body M of the endoscope. In a condition where the adaptor AD is coupled with the main body M of the endoscope as described above, the control knob is turned to move the rack R, thereby moving the movable frame back and forth by way of the wire WM.

The endoscope of the type which is configured so as to perform focusing by moving the lens components disposed in the leading end adaptor type objective optical system as described above has not only a defect that it can hardly have high operability and a compact size, but also another defect that it allows aberrations to be aggravated, a field angle thereof to be varied remarkably and hindrance to be caused for observation when the lens components are moved for a long distance.

Further, the conventional endoscope described above uses an aperture stop having a diameter which is kept fixed for focusing. Therefore, this endoscope provides brightness insufficient for observation of an object located at a long distance when the diameter of the aperture stop is small, for example, to obtain a large depth of field for observing an object located at a short distance. When the diameter of the aperture stop is large for obtaining brightness sufficient for observing an object located at a long distance, in contrast, the endoscope has a depth of field too small for observing an object located at a long distance and is therefore insufficient for practical use. On the other hand, an endoscope which is equipped with an automatic iris requires a large mechanism for controlling an aperture stop and is therefore undesirable as a practical endoscope.

SUMMARY OF THE INVENTION

A primary object of the present invention is to provide an objective optical system for endoscopes which is compact, features high operability and has a means for adjusting a distance to an object to be observed.

The objective optical system for endoscopes according to the present invention comprises a plurality of lens components and an aperture stop, and is characterized in that it permits adjusting the distance to the object to be observed by exchanging one of the lens components which is disposed in the vicinity of the aperture stop with another lens component having a focal length different from that of the former lens component.

FIG. 3 shows a sectional view illustrating a fundamental composition of a leading end adaptor type objective optical system for endoscopes which is preferred as a typical example of the objective optical system for endoscopes according to the present invention. As is seen from this drawing, the objective optical system for endoscopes according to the present invention consists of: an optical system which is to be disposed in a main body of an endoscope, and consists of an objective lens system 6 and an image transmission system 8 for transmitting an image 7 formed by the objective lens system 6; and an objective lens system 2 which is to be disposed in an adaptor, and consists of a plurality of lens components 3 and 5 disposed on an object side end surface of the optical system 1 as well as an aperture stop 4. The objective lens system 2 disposed in the adaptor is exchangeable with another adaptor side objective lens system 2' or 2" which comprises a lens component 5' or 5" different from the lens component 5 so that the endoscope can have a desired object distance.

Out of the adaptor side objective lens systems 2, 2' and 2", the objective lens system 2 uses a plane parallel plate 5 as the lens component disposed in the vicinity of the aperture stop 4 so that the object distance of the objective optical system which is determined dependently on a refractive power distribution between the lens components 3 is not influenced due to the lens component disposed in the vicinity of the aperture stop 4. In the adaptor side objective lens system 2', the lens component disposed in the vicinity of the aperture stop is a positive lens component 5' having a convex surface on the side of the aperture stop so as to obtain an object distance $L_n$ which is shorter than an object distance L determined dependently on the refractive power distribution in the lens system 3. Further, in the adaptor side objective lens system 2", the lens component disposed in the aperture stop is a negative lens component 5" which has a concave surface on the side of the aperture stop for obtaining an object distance $L_f$ which is longer than the object distance L determined dependently on the refractive power distribution in the lens components 3.

Furthermore, the adaptor side objective lens systems 2, 2' and 2" have field angles each nearly equal to a field angle of 2ω which is determined dependently on the refractive power distribution in the common lens components 3 and almost free from influence due to the lens components 5, 5' and 5" disposed in the vicinity of the aperture stop. In other words, the objective optical system for endoscopes according to the present invention has a field angle which is determined by a principal ray and scarecely varied by refraction due to the lens component 5, 5' or 5" since the principal ray has a height which can be regarded as zero on this lens component. Therefore, the field angle of the objective optical system for endoscopes according to the present invention can be kept constant even when the object distance is adjusted by varying a refractive power of the lens component disposed in the vicinity of the aperture stop.

When the adaptor side objective lens system 2, 2' or 2" is connected to the objective lens system 6 which is disposed in the main body M of the endoscope, a spacing between the objective lens systems is often deviated from a value predetermined therefor due to manufacturing errors within allowances specified for parts. For reducing an influence on the object distance L, $L_n$ or $L_f$ due to such a deviation of the spacing, it is desirable to configure the objective lens system 6 which is to be disposed in the main body M of the endoscope so as to form an image 7 at a location of a rear focal point of the objective lens system 6. In other words, it is desirable that a light bundle emerging from the adaptor side objective lens system 2, 2' or 2" is composed of rays which are parallel with one another.

As is understood from the foregoing description, the objective optical system for endoscopes according to the present invention consists of a plurality of lens components 3, 5, 6 and an aperture stop 4 as illustrated in FIG. 3. Speaking more concretely, the objective optical system for endoscopes according to the present invention consists of: the adaptor side objective lens system which is composed of the lens components 3 and 5, out of the plurality of lens components, and the aperture stop 4; and the objective lens system 6 to be disposed in the main body M of the endoscope which is composed of at least one lens component (two lens components in the objective lens system shown in FIG. 3). The object distance $L_f$ of the objective optical system for endoscopes according to the present invention is changed to a different object distance $L_n$ or $L_f$ by exchanging the lens component 5 which is disposed in the vicinity of the aperture stop 4 with the lens component 5' or 5" having a focal length different from that of the lens component 5.

For obtaining a light bundle composed of rays which are nearly parallel with one another, it is desirable to select, within the range defined below, a distance $\Delta f_{B6}$ as measured from a paraxial image point 7 to a rear focal point of the objective lens system 6 which is disposed in the main body M of the endoscope (a rear optical unit which is composed of the lens components disposed on the emergence side of the exchangeable lens component 5 disposed in the vicinity of the aperture stop 4):

$$50 \times f_6^2 \div 1000 \geq |\Delta f_{B6}|$$

This formula can be transformed as follows:

$$|\Delta f_{B6}/f_6^2| \leq 0.05$$

wherein the reference symbol $f_6$ represents a focal length of the objective lens system 6 to be disposed in the main body M of the endoscope (the rear optical unit which is composed of the lens components disposed on the emergence side of the exchangeable lens component 5 disposed in the vicinity of the aperture stop 4).

If $\Delta f_{B6}$ is large enough to exceed the range defined by the above-mentioned condition, a light bundle which is to be incident on the objective lens system 6 disposed in the main body M of the endoscope will undesirably be divergent or convergent.

When a convergent light bundle is to be incident on the objective lens 6, the spacing between the adaptor side objective lens system 2, 2' or 2" and the objective lens system 6 disposed in the main body M of the endoscope will be narrower than the predetermined value and the objective optical system for endoscopes will be focused on the object distance $L_f$ which is longer than the predetermined object distance L. When a divergent light bundle is to be incident on the objective lens system 6, in contrast, the spacing will be larger than the predetermined value and the objective optical system for endoscopes will undesirably be focused on an object distance which is shorter than the predetermined object distance L.

When a light bundle which is composed of rays nearly parallel with one another is to be incident on the objective lens system 6, the object distance L shown in FIG. 3 will be nearly coincident with a distance as measured from a principal point to a front focal point of the adaptor side objective lens system 2 (i.e., the lens components 3). When the lens component 5 which is disposed in the vicinity of the aperture stop 4 is exchanged with the lens component 5' or 5", the objective optical system is focused on an object distance described below:

When a focal length of the lens components 3 is represented by $f_3$, a front focal point of the adaptor side objective lens system 2' or 2" is designated by $f_{F2}$, a focal length of the lens component 5' or 5" is denoted by $f_5$ and a distance as measured from a principal point of the lens components 3 to a principal point of the lens component 5' or 5" is represented by d, the adaptor side objective lens system 2' or 2" has a focal length $f_2$ which is expressed by the following formula (1):

$$f_2 = f_3 \cdot f_5/(f_5 - f_3 - d) \tag{1}$$

Further, the front focal point $f_{F3}$ on an object distance is expressed by the following formula (2):

$$f_{F3} = f_2\{(f_5 - d)/f_5\} \tag{2}$$

However, since the objective optical system for endoscopes actually has an object distance which is as measured from a first surface thereof to an object to be observed, the object distance can be expressed by the following formula (2'):

$$f_{F3} = f_2\{(f_5 - d)/f_5\} - d' \tag{2'}$$

wherein the reference symbol d' represents a distance as measured from a front principal point H of the objective optical system 2' or 2" to the first surface of the objective optical system for endoscopes.

In this case, the object distance is changed by varying the focal length $f_5$ of the lens component which is disposed in the vicinity of the aperture stop arranged in the leading end adaptor. That is to say, the following formula (3) is obtained from the above-mentioned formula (2'):

$$f_5 = d \cdot f_2/(f_2 - f_{F3} - d') \tag{3}$$

In this case, the field angle 2ω is scarecely varied. That is to say, the focal length $f_2$ of the objective lens system 2, 2' or 2" which comprises the lens component 5, 5' or 5" as a whole is scarecely varied. When the lens component 5' or 5" is disposed with a certain space from the aperture stop, however, the field angle 2ω is largely varied, or the focal length $f_2$ of the adaptor side objective lens system is varied. As a result, it is desirable that the lens component 5' or 5" is disposed in the vicinity of the aperture stop so that ω is allowed to be varied within a range of 15%.

Since relationship between an image height and a field angle of an ordinary objective optical system for endoscopes (a telecentric optical system) is expressed as h=f·sin θ, it is desirable that the objective optical system satisfies the following condition:

$$|\{\sin^{-1}(h/f) - \sin^{-1}(h/f')\}/\sin^{-1}(h/f)| \leq 0.15$$

wherein the reference symbol h represents a maximum image height in the objective optical system, the reference symbol f designates a total focal length of the lens components 3 and 5 of the adaptor lens unit and the objective lens system 6 which is disposed in the main body of the endoscope (a focal length of the objective optical system for endoscopes as a whole), and the reference symbol f' denotes a focal length of the objective optical system for endoscopes as a whole when the lens component 5 of the adaptor side objective lens system is exchanged with the lens component 5' or 5".

When the objective optical system for endoscopes is to be used for observing an object located at a short distance which is to be illuminated sufficiently brightly with a light bundle emerging from the light guide fiber bundle built in the inserting portion, it is desirable to enlarge an F number and a depth of field of the objective optical system by reducing the diameter of the aperture stop. When the objective optical system for endoscopes is to be used for observing an object located at a long distance which is to be illuminated with insufficient brightness, it is desirable to reduce the F number of the objective optical system by enlarging the diameter of the aperture stop.

DETAILED DESCRIPTION OF THE PREFERRED EMBODIMENTS

Now, the objective optical system for endoscopes according to the present invention will be described more detailedly below with reference to the preferred embodiments thereof illustrated in the accompanying drawings.

Figure 1:
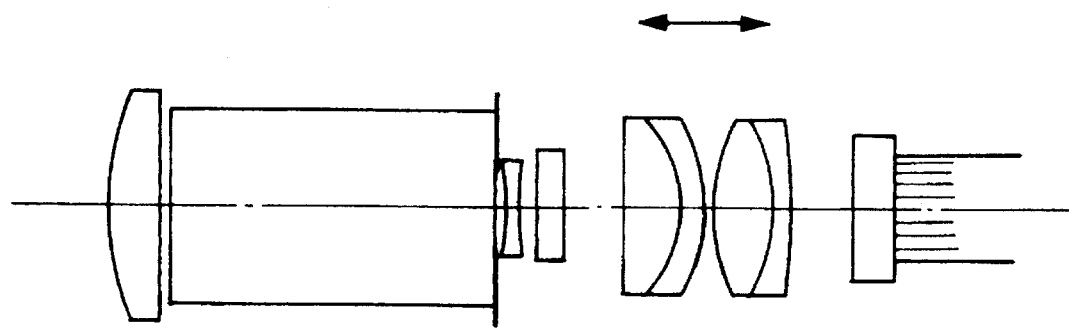
FIG. 1 shows a sectional view illustrating a composition of a conventional objective optical system for endoscopes.
Figure 2:
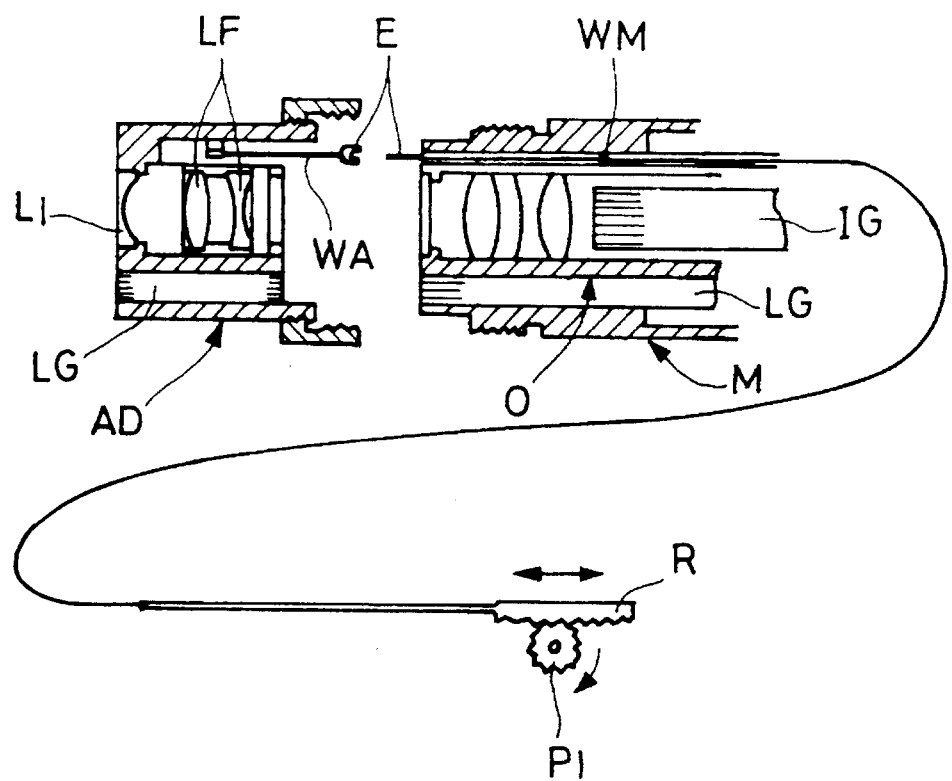
FIG. 2 shows a sectional view illustrating a composition of a conventional leading end adaptor type objective optical system for endoscopes.
Figure 3:
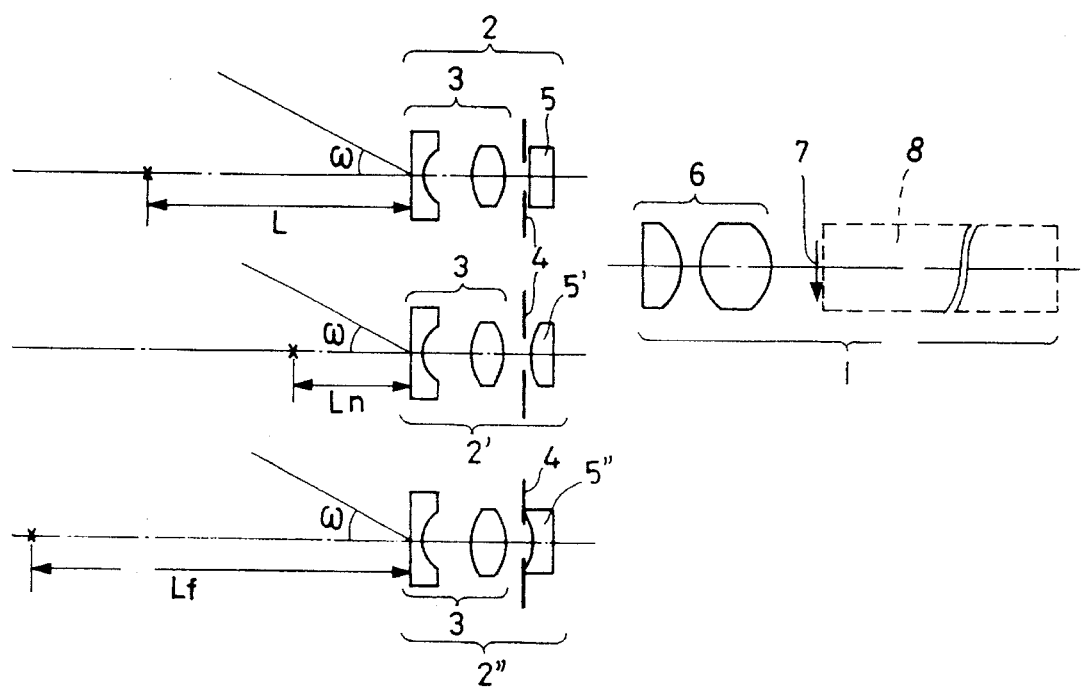
FIG. 3 shows a sectional view illustrating a fundamental composition of the objective optical system for endoscopes according to the present invention.
Figure 4:
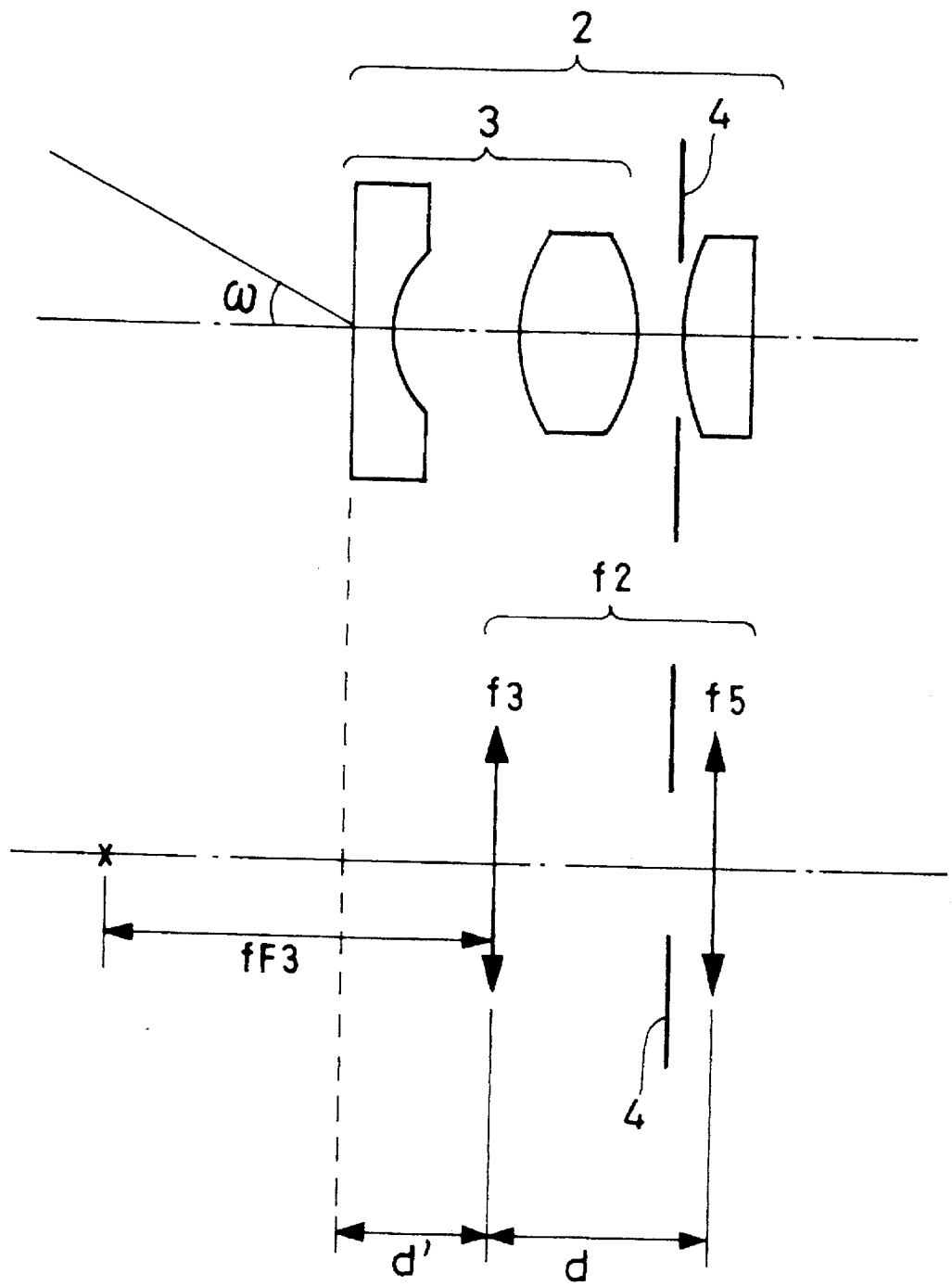
FIG. 4 shows a diagram illustrating relationship between compositions of the objective optical system for endoscopes according to the present invention and objective distances thereof.
Figure 5:
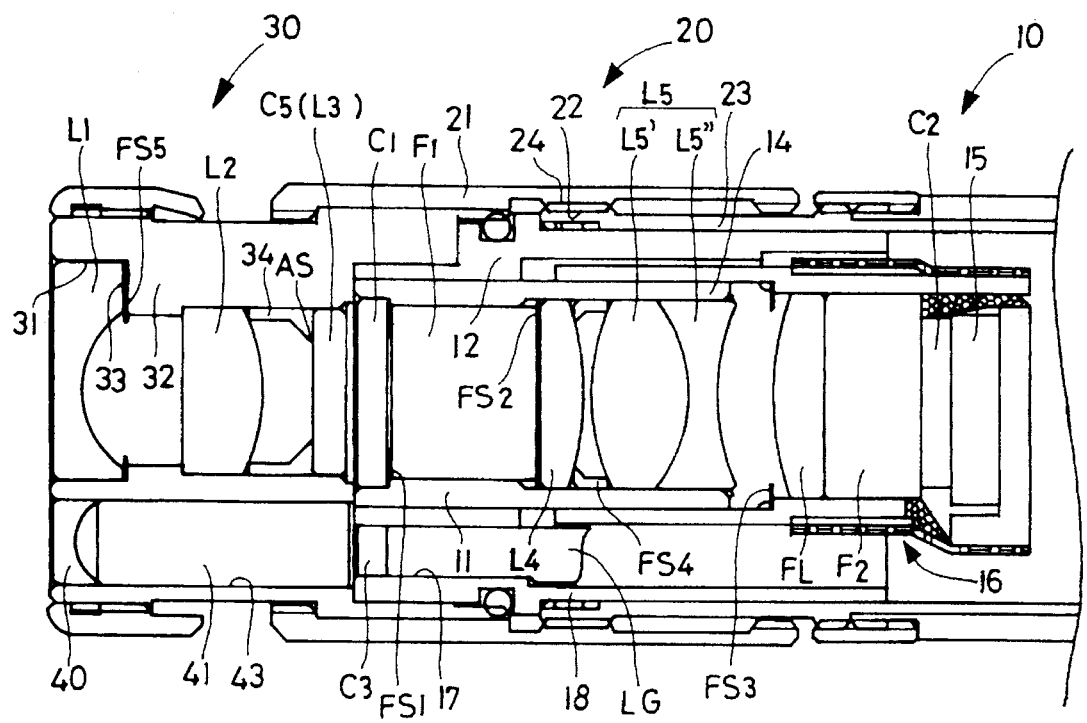
FIG. 5 and FIG. 6 show sectional views of a first embodiment of the present invention.

FIG. 5 shows a sectional view illustrating the composition of the first embodiment of the objective optical system for endoscopes according to the present invention, wherein a direct viewing type leading end adaptor which has a field angle of 100° is attached to a main body of an endoscope.

In this drawing, the reference numeral 10 represents the main body of the endoscope having a leading end (a master lens unit) 20 to which an adaptor unit 30 is attached. Disposed in a lens barrel which is sustained in the main body 10 are a cover glass plate $C_1$, an infrared light cutoff filter $F_1$ and a lens element $L_4$ which are arranged with flare stops $FS_1$ and $FS_2$ interposed therebetween, whereas a spacing tube serving also as a flare stop $FS_4$ and a lens component $L_5$ which consists of lens elements $L_5'$ and $L_5''$ are fixed on the image side. These members are inserted into an optical insertion hole 14 formed in a member 12 which composes an object side leading end of the lens barrel 11, and cemented or fixed therein.

Furthermore, fitted over an outside wall of the lens barrel 11 is an image pickup unit 16 in which a flare stop $FS_3$, a field lens FL, a low pass filter $F_2$, a cover glass plate $C_2$ and an image pickup element 15 are cemented or fixed. This image pickup unit 16 is fixed after it is shifted along the optical axis and a focal point of the objective lens system 6 which is disposed in the main body of the endoscope (the cover glass plate $C_1$, the infrared light cutoff filter $F_1$, the lens component $L_4$, the lens component $L_5$ consisting of the lens elements $L_5'$ and $L_5''$, the field lens FL, the low pass filter $F_2$, and the cover glass plate $C_2$) is adjusted.

Furthermore, formed in the leading end composing member 12 is a hole 17 into which a light guide fiber bundle LG having a cover glass plate $C_3$ cemented to a tip thereof is to be inserted. The light guide fiber bundle LG has the other end which is to be connected to a light source by way of a universal cord (not shown) passing throughout the main body of the endoscope.

On the other hand, the leading end adaptor unit 30 is attached to a fixing member 21 of the leading end master lens unit 20 of the main body 10 of the endoscope by screwing male threads 24 of a fixing member 23 for the main body into tapping 22 of an adaptor fixing member 21. Further, a lens component $L_1$ which is used for composing the objective lens system 2 is cemented or fixed on the side of the leading end in an observation hole 31 formed in the leading end adaptor unit 30 with a flare stop FS made of a thin metal plate interposed between a surface 33 of an adaptor composing member 32 and the lens component $L_1$. On the side of the main body of the endoscope in the observation hole 31 formed in the adaptor unit 30, a lens component $L_2$, a spacing tube 34 serving also as an aperture stop AS and a cover glass plate $C_5(L_3)$ are consecutively inserted and cemented or fixed.

Moreover, on the leading end, a light guide rod 41 on which an illumination lens 40 is mounted is cemented or fixed in an illumination system insertion hole 43 formed in the adaptor composing member 32.

Figure 6:
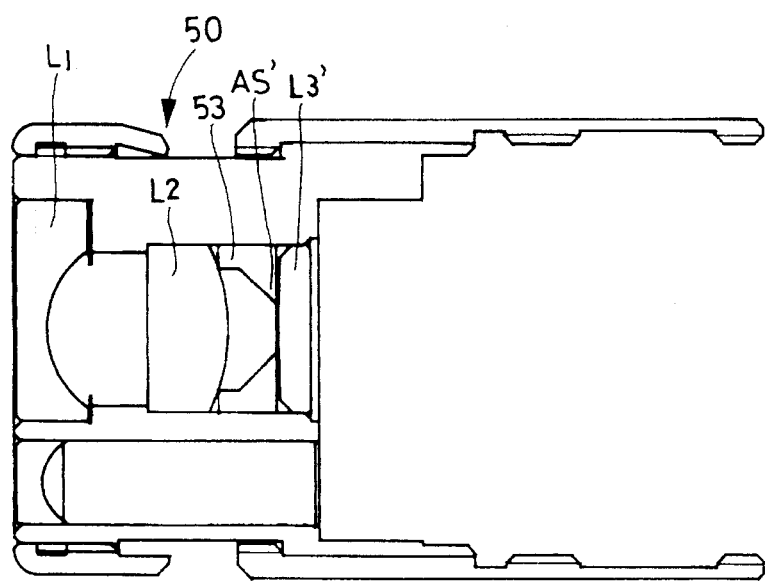

FIG. 6 shows a sectional view illustrating a direct viewing type leading end adaptor 50 for observing an object located at a short distance. Disposed in this adaptor unit 50 are a spacing tube 53 which has a narrowed portion for composing an aperture stop AS' having a small diameter, unlike the spacing tube 34 of the direct viewing type leading end adaptor unit 30 for observing the object located as the long distance shown in FIG. 5, lens components $L_1$ and $L_2$, and a lens component $L_3'$ (a focal point adjusting lens component) having a convex surface to be brought into contact with the aperture stop AS' of the spacing tube 53 which is adopted in place of the cover glass plate $C_5$ ($L_3$) used for the direct viewing type adaptor unit for observing the object located at the long distance. This lens component $L_3'$ is adopted for making the adaptor unit 50 suited for observing an object located at a distance which is shorter than that of the object to be observed by using the direct viewing type leading end adaptor for observing the object located at the long distance. In addition, the focal point adjusting lens component $L_3'$ shown in FIG. 6 is chamfered on the side of the spacing tube 53 so that surfaces having curvature can be discriminated.

Figure 7:
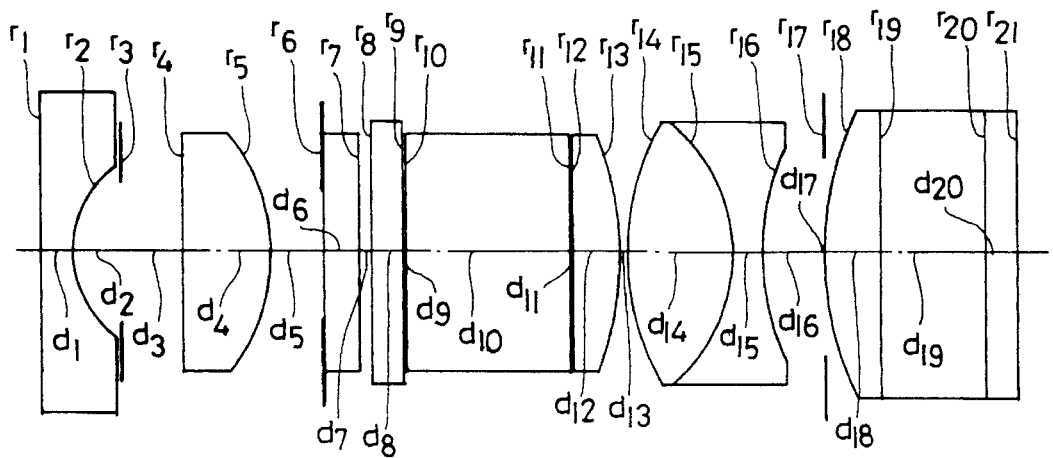
FIG. 7 and FIG. 8 show sectional views illustrating compositions of a first embodiment of the objective optical system for endoscopes according to the present invention.
Figure 8:
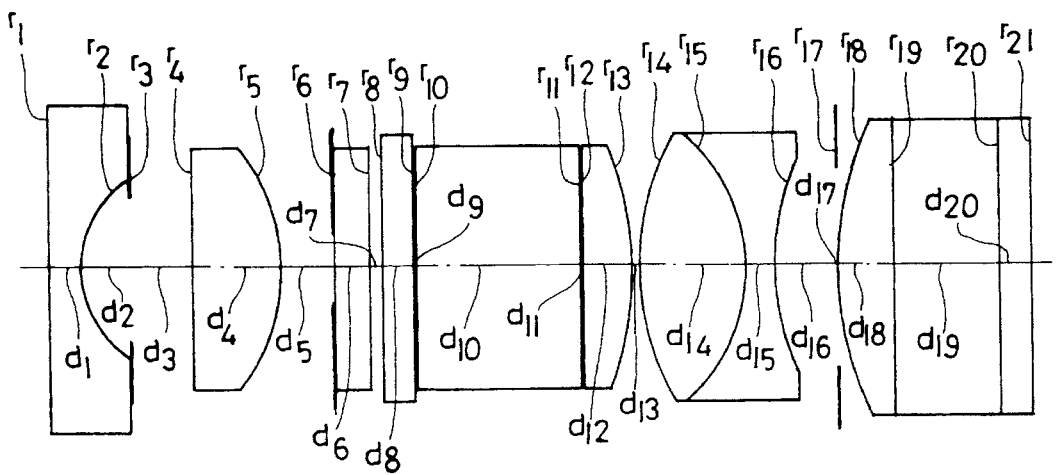

FIG. 7 and FIG. 8 show sectional views illustrating objective lens systems which are to be used in the first embodiment of the present invention. FIG. 7 shows a direct viewing type objective lens system for observing an object located at a long distance, whereas FIG. 8 shows a direct viewing type objective optical system for observing an object located at a short distance; these objective lens systems having the numerical data listed below:

Embodiment 1 for observing object at long distance
f=1.000, image height=0.8088, $f_B$=0.021,
2ω=100.27°, object distance=−42.7960

| | | |
|---|---|---|
| $r_1 = \infty$ | | |
| $d_1 = 0.2853$ | $n_1 = 1.88300$ | $v_1 = 40.78$ |
| $r_2 = 0.8845$ | | |
| $d_2 = 0.4280$ | | |
| $r_3 = \infty$ | | |
| $d_3 = 0.5492$ | | |
| $r_4 = \infty$ | | |
| $d_4 = 0.7846$ | $n_2 = 1.63930$ | $v_2 = 44.88$ |
| $r_5 = -1.5449$ | | |
| $d_5 = 0.4636$ | | |
| $r_6 = \infty$ (stop) | | |
| $d_6 = 0.3210$ | $n_3 = 1.88300$ | $v_3 = 40.78$ |
| $r_7 = \infty$ | | |
| $d_7 = 0.1070$ | | |
| $r_8 = \infty$ | | |
| $d_8 = 0.2853$ | $n_4 = 1.88300$ | $v_4 = 40.78$ |
| $r_9 = \infty$ | | |
| $d_9 = 0.0214$ | | |
| $r_{10} = \infty$ | | |
| $d_{10} = 1.4265$ | $n_5 = 1.52000$ | $v_5 = 74.00$ |
| $r_{11} = \infty$ | | |

-continued

| | | |
|---|---|---|
| $d_{11} = 0.0214$ | | |
| $r_{12} = \infty$ | | |
| $d_{12} = 0.4280$ | $n_6 = 1.62280$ | $v_6 = 57.06$ |
| $r_{13} = -2.5678$ | | |
| $d_{13} = 0.0713$ | | |
| $r_{14} = 2.1897$ | | |
| $d_{14} = 0.9272$ | $n_7 = 1.65844$ | $v_7 = 50.86$ |
| $r_{15} = -1.3966$ | | |
| $d_{15} = 0.2710$ | $n_8 = 1.75520$ | $v_8 = 27.51$ |
| $r_{16} = 2.1897$ | | |
| $d_{16} = 0.5421$ | | |
| $r_{17} = \infty$ | | |
| $d_{17} = 0.0000$ | | |
| $r_{18} = 2.7832$ | | |
| $d_{18} = 0.4993$ | $n_9 = 1.77250$ | $v_9 = 49.66$ |
| $r_{19} = \infty$ | | |
| $d_{19} = 0.9344$ | $n_{10} = 1.54814$ | $v_{10} = 45.78$ |
| $r_{20} = \infty$ | | |
| $d_{20} = 0.2853$ | $n_{11} = 1.52287$ | $v_{11} = 59.89$ |
| $r_{21} = \infty$ | | |
| $|\Delta f_{B6}/f_6^2| = 0.0031524674$ | | | for observing object at short distance
f=1.000, image height=0.8141, $f_B$=0.011,
2ω=100.34°, object distance=−10.3374

| | | |
|---|---|---|
| $r_1 = \infty$ | | |
| $d_1 = 0.2872$ | $n_1 = 1.88300$ | $v_1 = 40.78$ |
| $r_2 = 0.8902$ | | |
| $d_2 = 0.4307$ | | |
| $r_3 = \infty$ | | |
| $d_3 = 0.5528$ | | |
| $r_4 = \infty$ | | |
| $d_4 = 0.7897$ | $n_2 = 1.63930$ | $v_2 = 44.88$ |
| $r_5 = -1.5549$ | | |
| $d_5 = 0.4666$ | | |
| $r_6 = 68.4235$ (stop) | | |
| $d_6 = 0.3230$ | $n_3 = 1.88300$ | $v_3 = 40.78$ |
| $r_7 = \infty$ | | |
| $d_7 = 0.1077$ | | |
| $r_8 = \infty$ | | |
| $d_8 = 0.2872$ | $n_4 = 1.88300$ | $v_4 = 40.78$ |
| $r_9 = \infty$ | | |
| $d_9 = 0.0215$ | | |
| $r_{10} = \infty$ | | |
| $d_{10} = 1.4358$ | $n_5 = 1.52000$ | $v_5 = 74.00$ |
| $r_{11} = \infty$ | | |
| $d_{11} = 0.0215$ | | |
| $r_{12} = \infty$ | | |
| $d_{12} = 0.4307$ | $n_6 = 1.62280$ | $v_6 = 57.06$ |
| $r_{13} = -2.5844$ | | |
| $d_{13} = 0.0718$ | | |
| $r_{14} = 2.2039$ | | |
| $d_{14} = 0.9332$ | $n_7 = 1.65844$ | $v_7 = 50.86$ |
| $r_{15} = -1.4056$ | | |
| $d_{15} = 0.2728$ | $n_8 = 1.75520$ | $v_8 = 27.51$ |
| $r_{16} = 2.2039$ | | |
| $d_{16} = 0.5456$ | | |
| $r_{17} = \infty$ | | |
| $d_{17} = 0.0000$ | | |
| $r_{18} = 2.8011$ | | |
| $d_{18} = 0.5025$ | $n_9 = 1.77250$ | $v_9 = 49.66$ |
| $r_{19} = \infty$ | | |
| $d_{19} = 0.9404$ | $n_{10} = 1.54814$ | $v_{10} = 45.78$ |
| $r_{20} = \infty$ | | |
| $d_{20} = 0.2872$ | $n_{11} = 1.52287$ | $v_{11} = 59.89$ |
| $r_{21} = \infty$ | | |
| $|\Delta f_{B6}/f_6^2| = 0.0047572483$ | | |
| $|\{\sin^{-1}(h/f) - \sin^{-1}(h/f')\}/\sin^{-1}(h/f)| = 0.0006981151$ | | | wherein the reference symbols $r_1, r_2, \ldots$ represent radii of curvature on surfaces of the respective lens elements, the reference symbols $d_1, d_2, \ldots$ designate airspaces reserved between the surfaces of the respective lens elements, the reference symbols $n_1, n_2, \ldots$ denote refractive indices of the respective optical elements, and the reference symbols $v_1$, $v_2, \ldots$ represent Abbe's numbers of the respective optical elements.

In the first embodiment of the objective optical system for endoscopes according to the present invention described above, the focal point adjusting lens component which is to be used for observing the object located at the long distance has a planar surface $r_6$, whereas the focal point adjusting lens component which is to be adopted for observing the object located at short distance has a convex surface $r_6$.

Figure 9:
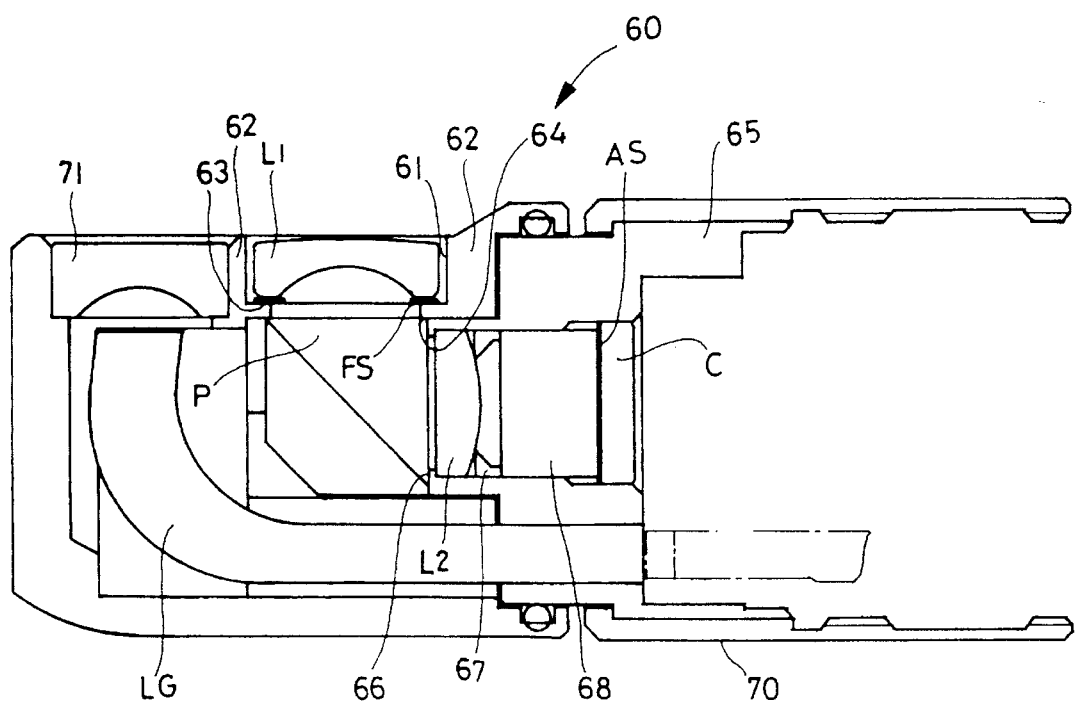
FIG. 9 and FIG. 10 show sectional views illustrating structures of a second embodiment of the present invention.
Figure 10:
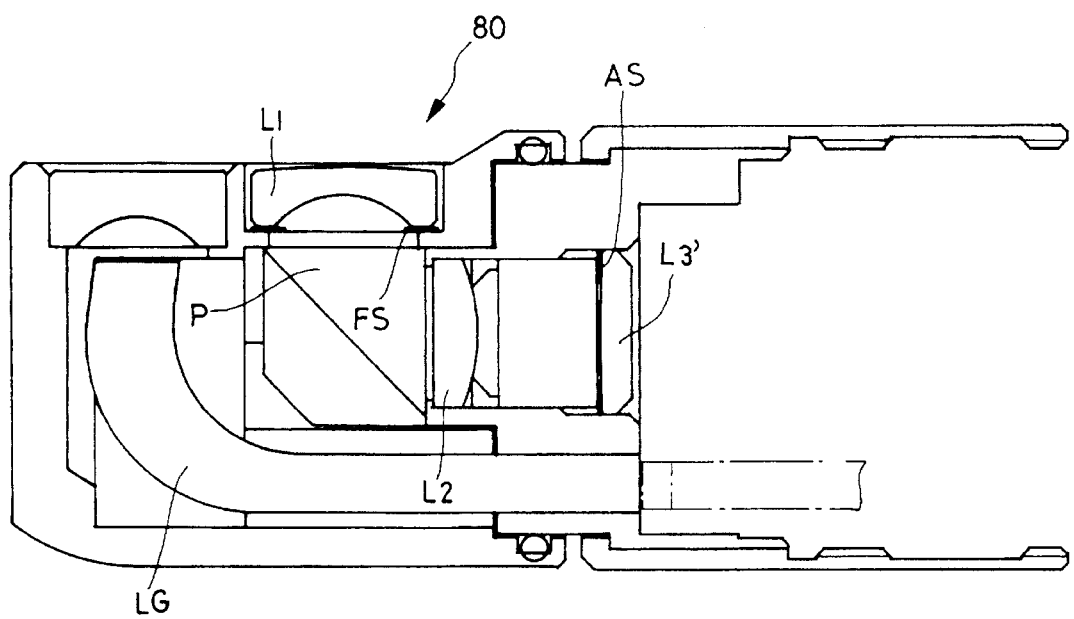

FIG. 9 and FIG. 10 show sectional views illustrating the second embodiment of the present invention. Out of these drawings, FIG. 9 shows a side viewing type leading end adaptor which is to be used for observing an object located at a long distance and has a field angle of 100°, whereas FIG. 10 shows a side viewing type leading end adaptor which is to be employed for observing an object located at a short distance.

A leading end adaptor unit 60 shown in FIG. 9 comprises: a lens component $L_1$, which is used for composing an objective lens system 2 to be disposed on an adaptor unit, cemented or fixed in an observation hole 61 formed on one side of a longitudinal centerline thereof with a flare stop 63 made of a thin metal plate interposed between a surface 63 of an adaptor composing member 62 and the lens component $L_1$; a viewing direction changing prism P which is supported, under the observation hole 61, by a surface 64 of the adaptor composing member 62, a side wall (not shown) of an observation window and a tip 66 of a lens barrel 65, and cemented or fixed to these members; and a lens component $L_2$, a spacing the 67 serving also as a flare stop, optical path adjusting glass member 68, an aperture stop AS made of a thin metal plate and a cover glass plate C which are inserted into the lens barrel 65 in an order from the side of the tip thereof and cemented or fixed to the lens barrel 65. The optical path adjusting glass member 68 is used for reserving a space for an adaptor side fixing member 70 over the lens barrel 65.

Further, an illumination lens 71 is cemented or fixed in an illumination system insertion hole formed in the adaptor composing member 62 and a light guide fiber bundle LG extends from a location in the vicinity of a concave surface of the illumination lens 71 to a location corresponding to an illumination window formed in the leading end of the main body of the endoscope and cemented or fixed to the light guide fiber bundle insertion hole formed in the lens barrel 65.

A side viewing type leading end adaptor unit 80 for observing an object located at a short distance shown in FIG. 10 uses, in place of the aperture stop adopted in the side viewing type leading end adaptor unit 60, an aperture stop which has a small diameter for observing an object located at a short distance so that the objective optical system for endoscopes has a large depth of field. Further, this leading end adaptor unit 80 adopts a focal point adjusting lens component $L_3'$, in place of the cover glass plate C of the side viewing type leading end adaptor 60 for observing the object located at the long distance, which adjusts the focal point so that the leading end adaptor unit 80 is suited for observing an object located at a distance shorter than the object distance of the side viewing type leading end adaptor unit 60 for observing the object located at the long distance. In the second embodiment also, the focal point adjusting lens component $L_3'$ is chamfered on the side of the main body of the endoscope for facilitating discrimination of surfaces having curvature.

Figure 11:
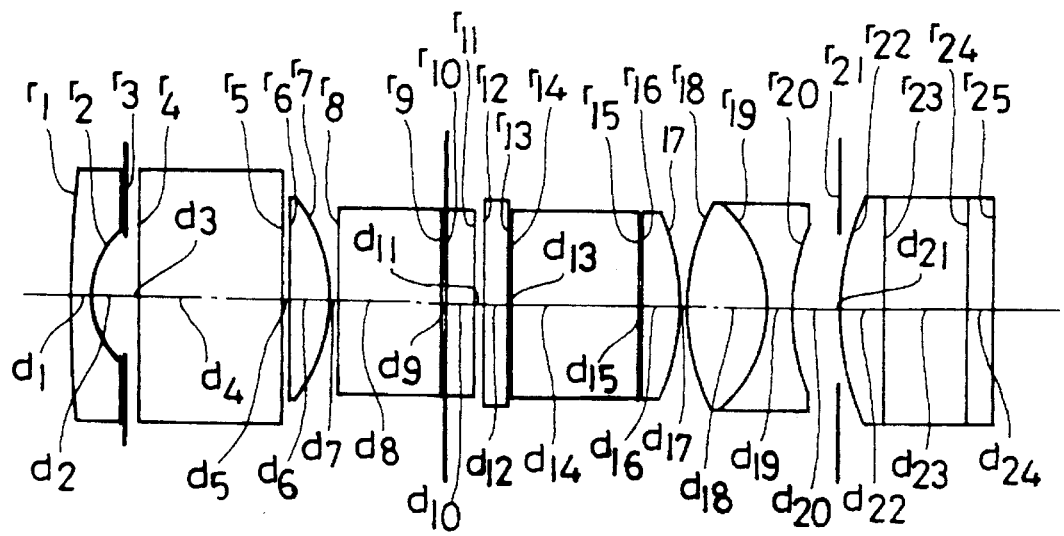
FIG. 11 and FIG. 12 show sectional views illustrating compositions of an objective optical system for endoscopes which is to be used in the second embodiment of the present invention.
Figure 12:
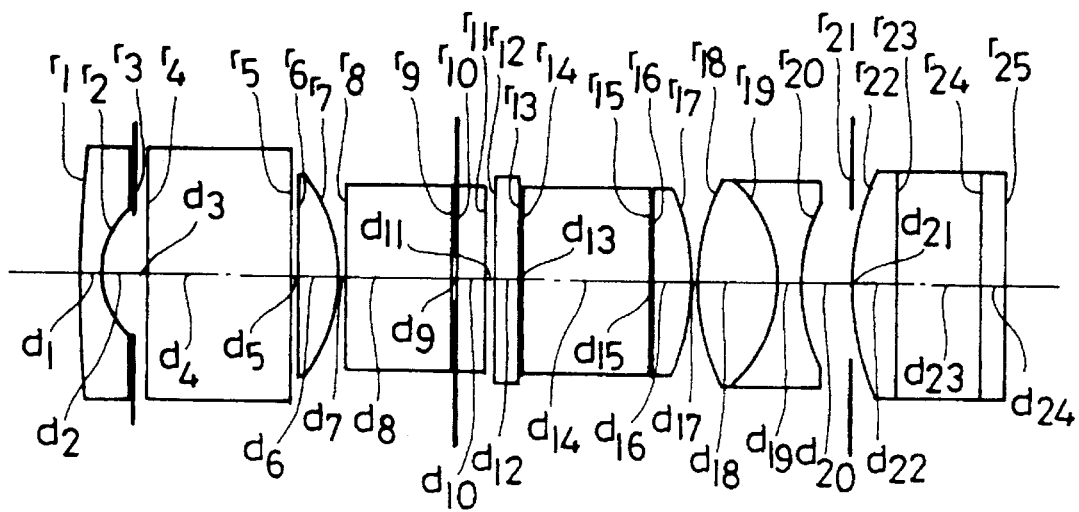

The objective optical system for endoscopes preferred as the second embodiment has the compositions illustrated in FIG. 11 and FIG. 12, and numerical data which are listed below:

Embodiment 2 for observing object at long distance
f=1.000, image height=0.8265, $f_B$=0.012,
2ω=99.368°, object distance=−8.7464

| | | |
|---|---|---|
| $r_1 = 13.8491$ | | |
| $d_1 = 0.2551$ | $n_1 = 1.88300$ | $v_1 = 40.78$ |
| $r_2 = 0.9446$ | | |
| $d_2 = 0.3644$ | | |
| $r_3 = \infty$ | | |
| $d_3 = 0.1458$ | | |
| $r_4 = \infty$ | | |
| $d_4 = 1.6764$ | $n_2 = 1.88300$ | $v_2 = 40.78$ |
| $r_5 = \infty$ | | |
| $d_5 = 0.0802$ | | |
| $r_6 = \infty$ | | |
| $d_6 = 0.4665$ | $n_3 = 1.60342$ | $v_3 = 38.01$ |
| $r_7 = -1.6603$ | | |
| $d_7 = 0.0729$ | | |
| $r_8 = \infty$ | | |
| $d_8 = 1.2391$ | $n_4 = 1.88300$ | $v_4 = 40.78$ |
| $r_9 = \infty$ | | |
| $d_9 = 0.0219$ | | |
| $r_{10} = \infty$ (stop) | | |
| $d_{10} = 0.3280$ | $n_5 = 1.88300$ | $v_5 = 40.78$ |
| $r_{11} = \infty$ | | |
| $d_{11} = 0.1093$ | | |
| $r_{12} = \infty$ | | |
| $d_{12} = 0.2915$ | $n_6 = 1.88300$ | $v_6 = 40.78$ |
| $r_{13} = \infty$ | | |
| $d_{13} = 0.0219$ | | |
| $r_{14} = \infty$ | | |
| $d_{14} = 1.4577$ | $n_7 = 1.52000$ | $v_7 = 74.00$ |
| $r_{15} = \infty$ | | |
| $d_{15} = 0.0219$ | | |
| $r_{16} = \infty$ | | |
| $d_{16} = 0.4373$ | $n_8 = 1.62280$ | $v_8 = 57.06$ |
| $r_{17} = -2.6239$ | | |
| $d_{17} = 0.0729$ | | |
| $r_{18} = 2.2376$ | | |
| $d_{18} = 0.9475$ | $n_9 = 1.65844$ | $v_9 = 50.86$ |
| $r_{19} = -1.4271$ | | |
| $d_{19} = 0.2770$ | $n_{10} = 1.75520$ | $v_{10} = 27.51$ |
| $r_{20} = 2.2376$ | | |
| $d_{20} = 0.5539$ | | |
| $r_{21} = \infty$ | | |
| $d_{21} = 0.0000$ | | |
| $r_{22} = 2.8440$ | | |
| $d_{22} = 0.5102$ | $n_{11} = 1.77250$ | $v_{11} = 49.66$ |
| $r_{23} = \infty$ | | |
| $d_{23} = 0.9548$ | $n_{12} = 1.54814$ | $v_{12} = 45.78$ |
| $r_{24} = \infty$ | | |
| $d_{24} = 0.2915$ | $n_{13} = 1.52287$ | $v_{13} = 59.89$ |
| $r_{25} = \infty$ | | |
| $|\Delta f_{B6}/f_6^2| = 0.0046141247$ | | | for observing object at short distance
f=1.000, image height=0.8314, $f_B$= 0.013,
2ω=99.568°, object distance=−5.1320

| | | |
|---|---|---|
| $r_1 = 13.9304$ | | |
| $d_1 = 0.2566$ | $n_1 = 1.88300$ | $v_1 = 40.78$ |
| $r_2 = 0.9501$ | | |
| $d_2 = 0.3666$ | | |
| $r_3 = \infty$ | | |
| $d_3 = 0.1466$ | | |
| $r_4 = \infty$ | | |
| $d_4 = 1.6862$ | $n_2 = 1.88300$ | $v_2 = 40.78$ |
| $r_5 = \infty$ | | |
| $d_5 = 0.0806$ | | |
| $r_6 = \infty$ | | |
| $d_6 = 0.4692$ | $n_3 = 1.60342$ | $v_3 = 38.01$ |

-continued

| | | |
|---|---|---|
| $r_7 = -1.6701$ | | |
| $d_7 = 0.0733$ | | |
| $r_8 = \infty$ | | |
| $d_8 = 1.2463$ | $n_4 = 1.88300$ | $v_4 = 40.78$ |
| $r_9 = \infty$ | | |
| $d_9 = 0.0220$ | | |
| $r_{10} = \infty$ (stop) | | |
| $d_{10} = 0.3299$ | $n_5 = 1.88300$ | $v_5 = 40.78$ |
| $r_{11} = -90.7705$ | | |
| $d_{11} = 0.1100$ | | |
| $r_{12} = \infty$ | | |
| $d_{12} = 0.2933$ | $n_6 = 1.88300$ | $v_6 = 40.78$ |
| $r_{13} = \infty$ | | |
| $d_{13} = 0.0220$ | | |
| $r_{14} = \infty$ | | |
| $d_{14} = 1.4663$ | $n_7 = 1.52000$ | $v_7 = 74.00$ |
| $r_{15} = \infty$ | | |
| $d_{15} = 0.0220$ | | |
| $r_{16} = \infty$ | | |
| $d_{16} = 0.4399$ | $n_8 = 1.62280$ | $v_8 = 57.06$ |
| $r_{17} = -2.6393$ | | |
| $d_{17} = 0.0733$ | | |
| $r_{18} = 2.2507$ | | |
| $d_{18} = 0.9531$ | $n_9 = 1.65844$ | $v_9 = 50.86$ |
| $r_{19} = -1.4355$ | | |
| $d_{19} = 0.2786$ | $n_{10} = 1.75520$ | $v_{10} = 27.51$ |
| $r_{20} = 2.2507$ | | |
| $d_{20} = 0.5572$ | | |
| $r_{21} = \infty$ | | |
| $d_{21} = 0.0000$ | | |
| $r_{22} = 2.8607$ | | |
| $d_{22} = 0.5132$ | $n_{11} = 1.77250$ | $v_{11} = 49.66$ |
| $r_{23} = \infty$ | | |
| $d_{23} = 0.9604$ | $n_{12} = 1.54814$ | $v_{12} = 45.78$ |
| $r_{24} = \infty$ | | |
| $d_{24} = 0.2933$ | $n_{13} = 1.52287$ | $v_{13} = 59.89$ |
| $r_{25} = \infty$ | | |
| $|\Delta f_{B6}/f_6^2| = 0.0044021807$ | | |
| $|\{\sin^{-1}(h/f) - \sin^{-1}(h/f')\}/\sin^{-1}(h/f)| = 0.0020127204$ | | |

In the second embodiment, a surface $r_{11}$ for observing the object located at the long distance is planar, whereas a surface $r_{11}$ for observing the object located at the short distance is convex.

Figure 13:
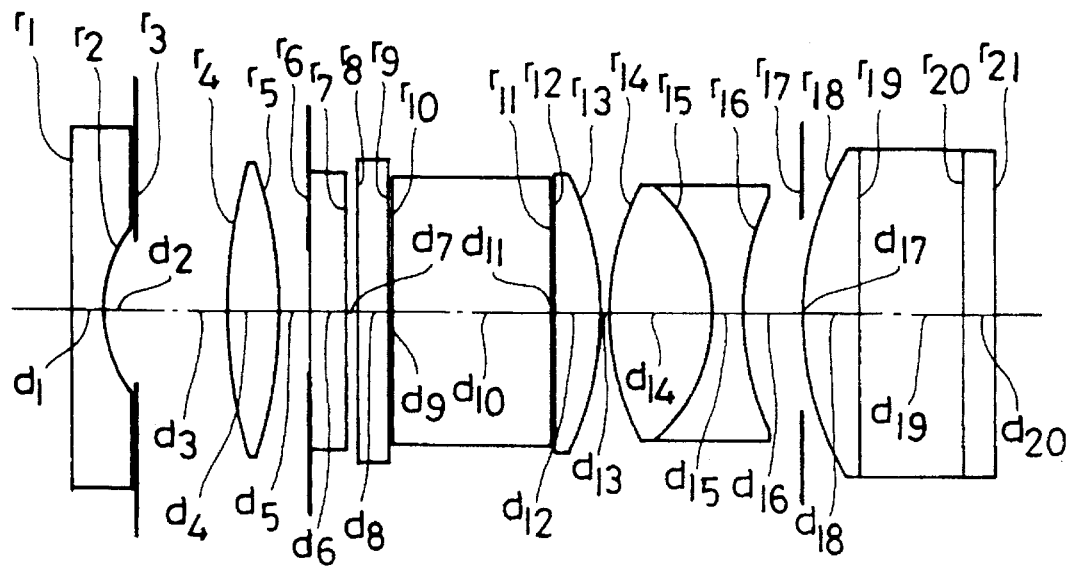
FIG. 13 and FIG. 14 show sectional views illustrating compositions of an objective optical system for endoscopes which is preferred as a third embodiment of the present invention.
Figure 14:
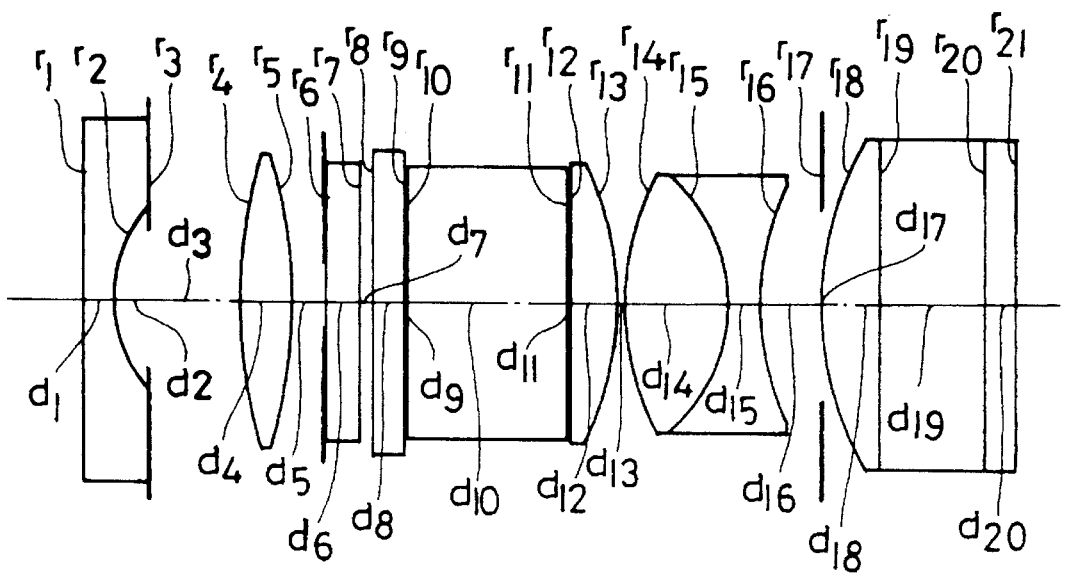

FIG. 13 and FIG. 14 show sectional views illustrating compositions of a direct viewing type objective optical system for endoscopes which is preferred as the third embodiment of the present invention. FIG. 13 shows a direct viewing type objective lens system for observing an object located at a long distance, whereas FIG. 14 shows a direct viewing type objective lens system for observing an object located at a short distance. These objective lens systems have numerical data which are listed below:

Embodiment 3 for observing object at long distance
f=1.000, image height=0.5108, $f_B$=−0.002,
2ω=58.996°, object distance=−31.5315

| | | |
|---|---|---|
| $r_1 = \infty$ | | |
| $d_1 = 0.1802$ | $n_1 = 1.51633$ | $v_1 = 64.15$ |
| $r_2 = 0.7423$ | | |
| $d_2 = 0.1802$ | | |
| $r_3 = \infty$ | | |
| $d_3 = 0.5135$ | | |
| $r_4 = 2.5468$ | | |
| $d_4 = 0.2973$ | $n_2 = 1.61700$ | $v_2 = 62.79$ |
| $r_5 = -2.5468$ | | |
| $d_5 = 0.1757$ | | |
| $r_6 = \infty$ (stop) | | |
| $d_6 = 0.2027$ | $n_3 = 1.88300$ | $v_3 = 40.78$ |
| $r_7 = \infty$ | | |
| $d_7 = 0.0676$ | | |

-continued

| | | |
|---|---|---|
| $r_8 = \infty$ | | |
| $d_8 = 0.1802$ | $n_4 = 1.88300$ | $v_4 = 40.78$ |
| $r_9 = \infty$ | | |
| $d_9 = 0.0135$ | | |
| $r_{10} = \infty$ | | |
| $d_{10} = 0.9009$ | $n_5 = 1.52000$ | $v_5 = 74.00$ |
| $r_{11} = \infty$ | | |
| $d_{11} = 0.0135$ | | |
| $r_{12} = \infty$ | | |
| $d_{12} = 0.2703$ | $n_6 = 1.62280$ | $v_6 = 57.06$ |
| $r_{13} = -1.6216$ | | |
| $d_{13} = 0.0450$ | | |
| $r_{14} = 1.3829$ | | |
| $d_{14} = 0.5856$ | $n_7 = 1.65844$ | $v_7 = 50.86$ |
| $r_{15} = -0.8820$ | | |
| $d_{15} = 0.1712$ | $n_8 = 1.75520$ | $v_8 = 27.51$ |
| $r_{16} = 1.3829$ | | |
| $d_{16} = 0.3423$ | | |
| $r_{17} = \infty$ | | |
| $d_{17} = 0.0000$ | | |
| $r_{18} = 1.7577$ | | |
| $d_{18} = 0.3153$ | $n_9 = 1.77250$ | $v_9 = 49.66$ |
| $r_{19} = \infty$ | | |
| $d_{19} = 0.5901$ | $n_{10} = 1.54814$ | $v_{10} = 45.78$ |
| $r_{20} = \infty$ | | |
| $d_{20} = 0.1802$ | $n_{11} = 1.52287$ | $v_{11} = 59.89$ |
| $r_{21} = \infty$ | | |
| $|\Delta f_{B6}/f_6^2| = 0.0095857258$ | | | for observing object at short distance
f=1.000, image height=0.5157, $f_B$=0.000,
2ω=58.984°, object distance=−8.6403

| | | |
|---|---|---|
| $r_1 = \infty$ | | |
| $d_1 = 0.1819$ | $n_1 = 1.51633$ | $v_1 = 64.15$ |
| $r_2 = 0.7494$ | | |
| $d_2 = 0.1819$ | | |
| $r_3 = \infty$ | | |
| $d_3 = 0.5184$ | | |
| $r_4 = 2.5712$ | | |
| $d_4 = 0.3001$ | $n_2 = 1.61700$ | $v_2 = 62.79$ |
| $r_5 = -2.5712$ | | |
| $d_5 = 0.1774$ | | |
| $r_6 = 28.3893$ (stop) | | |
| $d_6 = 0.2046$ | $n_3 = 1.88300$ | $v_3 = 40.78$ |
| $r_7 = \infty$ | | |
| $d_7 = 0.0682$ | | |
| $r_8 = \infty$ | | |
| $d_8 = 0.1819$ | $n_4 = 1.88300$ | $v_4 = 40.78$ |
| $r_9 = \infty$ | | |
| $d_9 = 0.0136$ | | |
| $r_{10} = \infty$ | | |
| $d_{10} = 0.9095$ | $n_5 = 1.52000$ | $v_5 = 74.00$ |
| $r_{11} = \infty$ | | |
| $d_{11} = 0.0136$ | | |
| $r_{12} = \infty$ | | |
| $d_{12} = 0.2729$ | $n_6 = 1.62280$ | $v_6 = 57.06$ |
| $r_{13} = -1.6371$ | | |
| $d_{13} = 0.0455$ | | |
| $r_{14} = 1.3961$ | | |
| $d_{14} = 0.5912$ | $n_7 = 1.65844$ | $v_7 = 50.86$ |
| $r_{15} = -0.8904$ | | |
| $d_{15} = 0.1728$ | $n_8 = 1.75520$ | $v_8 = 27.51$ |
| $r_{16} = 1.3961$ | | |
| $d_{16} = 0.3456$ | | |
| $r_{17} = \infty$ | | |
| $d_{17} = 0.0000$ | | |
| $r_{18} = 1.7744$ | | |
| $d_{18} = 0.3183$ | $n_9 = 1.77250$ | $v_9 = 49.66$ |
| $r_{19} = \infty$ | | |
| $d_{19} = 0.5957$ | $n_{10} = 1.54814$ | $v_{10} = 45.78$ |
| $r_{20} = \infty$ | | |
| $d_{20} = 0.1819$ | $n_{11} = 1.52287$ | $v_{11} = 59.89$ |
| $r_{21} = \infty$ | | |
| $|\Delta f_{B6}/f_6^2| = 0.0102203675$ | | |
| $|\{\sin^{-1}(h/f) - \sin^{-1}(h/f')\}/\sin^{-1}(h/f)| = 0.0002034036$ | | |

In the third embodiment of the present invention, a surface $r_6$ which is to be used for observing the object located at the long distance is planar and a surface $r_6$ which is to be employed for observing the object located at the short distance is convex.

Figure 15:
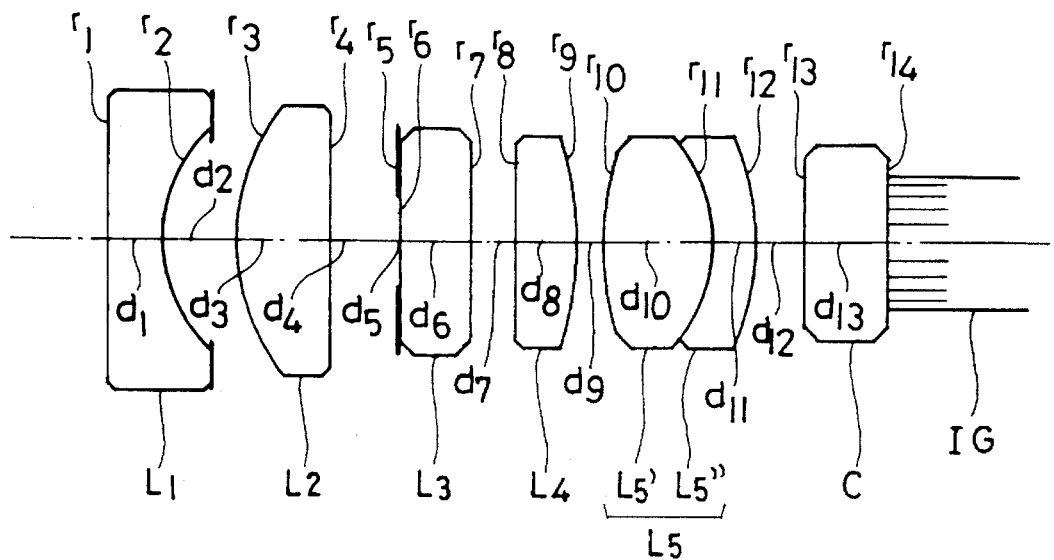
FIG. 15 and FIG. 16 show sectional views illustrating compositions of an objective optical system for endoscopes which is preferred as a fourth embodiment of the present invention.
Figure 16:
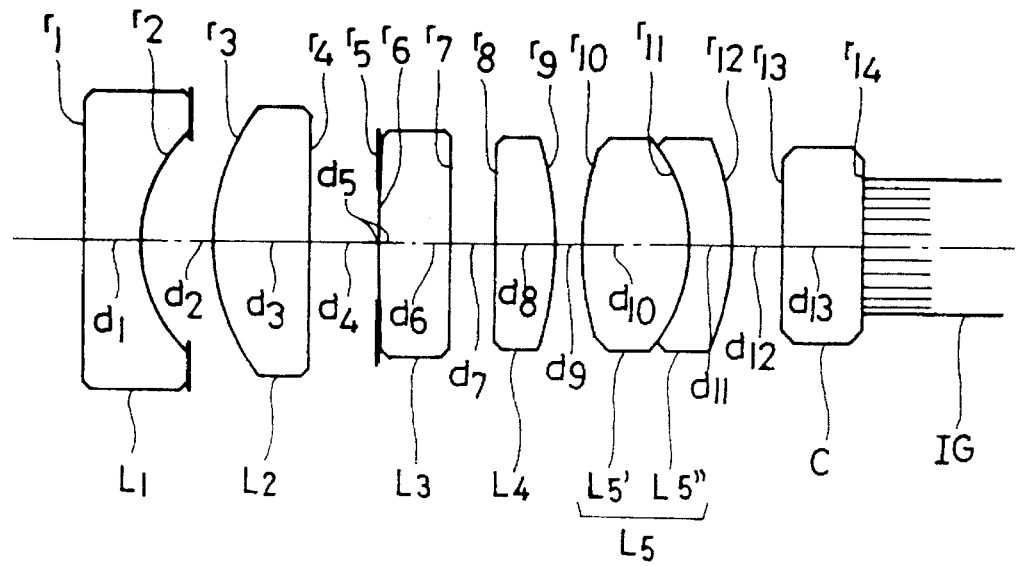

FIG. 15 and FIG. 16 show sectional views illustrating compositions of a leading end adaptor type objective optical system for endoscope having a field angle of 60° which is preferred as the fourth embodiment of the present invention, in which an optical fiber bundle is used as an image transmission system. FIG. 15 shows a sectional view illustrating the objective optical system for endoscopes in a condition where it is equipped with a direct viewing type adaptor for observing an object located at a long distance, whereas FIG. 16 shows a sectional view illustrating the objective optical system for endoscopes in another condition where it is equipped with a direct viewing type leading end adaptor for observing an object located at a short distance.

The fourth embodiment consists of: a leading end adaptor which is composed of a negative lens component $L_1$, a positive lens component $L_2$, an aperture stop AS and a focal point adjusting lens component $L_3$; a positive lens component $L_4$; a cemented lens component $L_5$ which is composed of a positive lens element $L_5'$ and a negative lens element $L_5''$; a cover glass plate C; an image guide IG made of an optical fiber bundle. In the objective optical system for endoscopes shown in FIG. 16, the adaptor which uses the focal point adjusting lens component $L_3$ is exchanged with another adaptor which uses a lens component $L_3''$ having a concave surface $r_6$ on the object side for observing an object located at a short distance and an aperture stop having a smaller diameter is adapted so that the objective optical system for endoscopes has a larger depth of field and permits observing an object located at a distance shorter than the object distance of the objective optical system shown in FIG. 15. The fourth embodiment of the objective optical system for endoscopes according to the present invention has the numerical data which are listed below:

Embodiment 4 for observing object at long distance
f=1.001, image height=0.4926, $f_B$=0.038,
2ω=59.652°, object distance=−71.8422

| | | |
|---|---|---|
| $r_1 = \infty$ | | |
| $d_1 = 0.4237$ | $n_1 = 1.88300$ | $v_1 = 40.78$ |
| $r_2 = 1.1197$ | | |
| $d_2 = 0.5614$ | | |
| $r_3 = 1.5074$ | | |
| $d_3 = 0.7415$ | $n_2 = 1.80518$ | $v_2 = 25.43$ |
| $r_4 = \infty$ | | |
| $d_4 = 0.5297$ | | |
| $r_5 = \infty$ (stop) | | |
| $d_5 = 0.0000$ | | |
| $r_6 = \infty$ | | |
| $d_6 = 0.5297$ | $n_3 = 1.51633$ | $v_3 = 64.15$ |
| $r_7 = \infty$ | | |
| $d_7 = 0.3390$ | | |
| $r_8 = \infty$ | | |
| $d_8 = 0.4555$ | $n_4 = 1.88300$ | $v_4 = 40.78$ |
| $r_9 = -2.6822$ | | |
| $d_9 = 0.2119$ | | |
| $r_{10} = 2.2574$ | | |
| $d_{10} = 0.8475$ | $n_5 = 1.60311$ | $v_5 = 60.70$ |
| $r_{11} = -1.1716$ | | |
| $d_{11} = 0.3178$ | $n_6 = 1.84666$ | $v_6 = 23.78$ |
| $r_{12} = -1.9513$ | | |
| $d_{12} = 0.3814$ | | |
| $r_{13} = \infty$ | | |
| $d_{13} = 0.6356$ | $n_7 = 1.51633$ | $v_7 = 64.15$ |
| $r_{14} = \infty$ | | |
| $|\Delta f_{B6}/f_6^2| = 0.0173816556$ | | | for observing object at short distance
f=0.999, image height=0.4936, $f_B$=0.049,
2ω=59.644°, object distance=−9.3406

| | | |
|---|---|---|
| $r_1 = \infty$ | | |
| $d_1 = 0.4246$ | $n_1 = 1.88300$ | $v_1 = 40.78$ |
| $r_2 = 1.1221$ | | |
| $d_2 = 0.5626$ | | |
| $r_3 = 1.5106$ | | |
| $d_3 = 0.7431$ | $n_2 = 1.80518$ | $v_2 = 25.43$ |
| $r_4 = \infty$ | | |
| $d_4 = 0.5308$ | | |
| $r_5 = \infty$ (stop) | | |
| $d_5 = 0.0000$ | | |
| $r_6 = 15.2686$ | | |
| $d_6 = 0.5308$ | $n_3 = 1.51633$ | $v_3 = 64.15$ |
| $r_7 = \infty$ | | |
| $d_7 = 0.3397$ | | |
| $r_8 = \infty$ | | |
| $d_8 = 0.4565$ | $n_4 = 1.88300$ | $v_4 = 40.78$ |
| $r_9 = -2.6879$ | | |
| $d_9 = 0.2123$ | | |
| $r_{10} = 2.2622$ | | |
| $d_{10} = 0.8493$ | $n_5 = 1.60311$ | $v_5 = 60.70$ |
| $r_{11} = -1.1741$ | | |
| $d_{11} = 0.3185$ | $n_6 = 1.84666$ | $v_6 = 23.78$ |
| $r_{12} = -1.9554$ | | |
| $d_{12} = 0.3822$ | | |
| $r_{13} = \infty$ | | |
| $d_{13} = 0.6369$ | $n_7 = 1.51633$ | $v_7 = 64.15$ |
| $r_{14} = \infty$ | | |
| $|\Delta f_{B6}/f_6^2| = 0.0224567287$ | | |
| $|\{\sin^{-1}(h/f) - \sin^{-1}(h/f')\}/\sin^{-1}(h/f)| = 0.0001341112$ | | |

In the fourth embodiment also, a surface $r_6$ to be used for observing the object located at the long distance is planar, whereas a surface $r_6$ for observing the object located at the short distance is convex.

Figure 17:
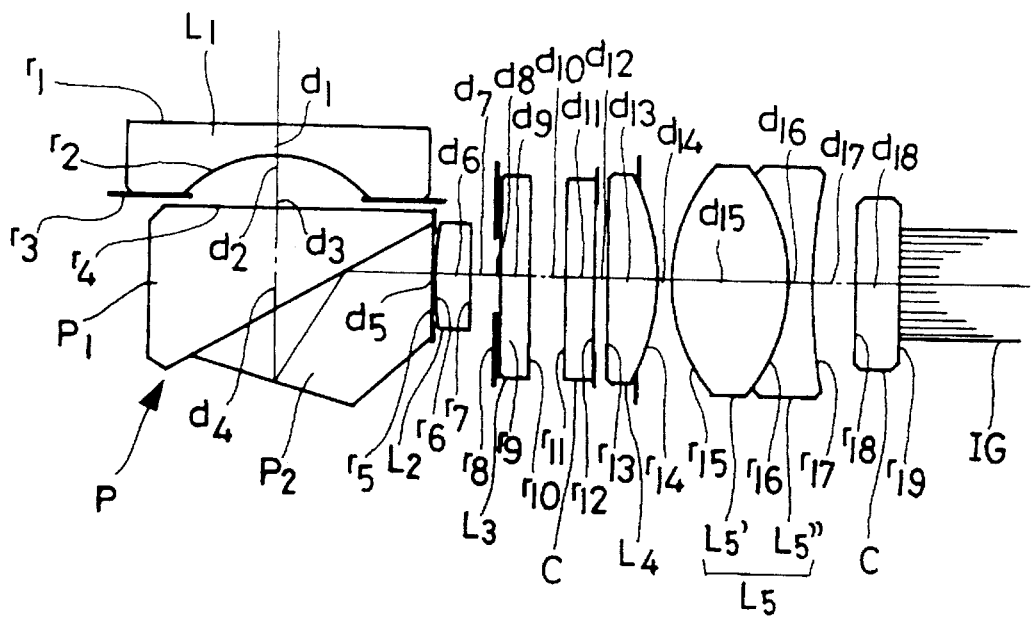
FIG. 17 and FIG. 18 show sectional views illustrating compositions of an objective optical system for endoscopes which is preferred as a fifth embodiment of the present invention.
Figure 18:
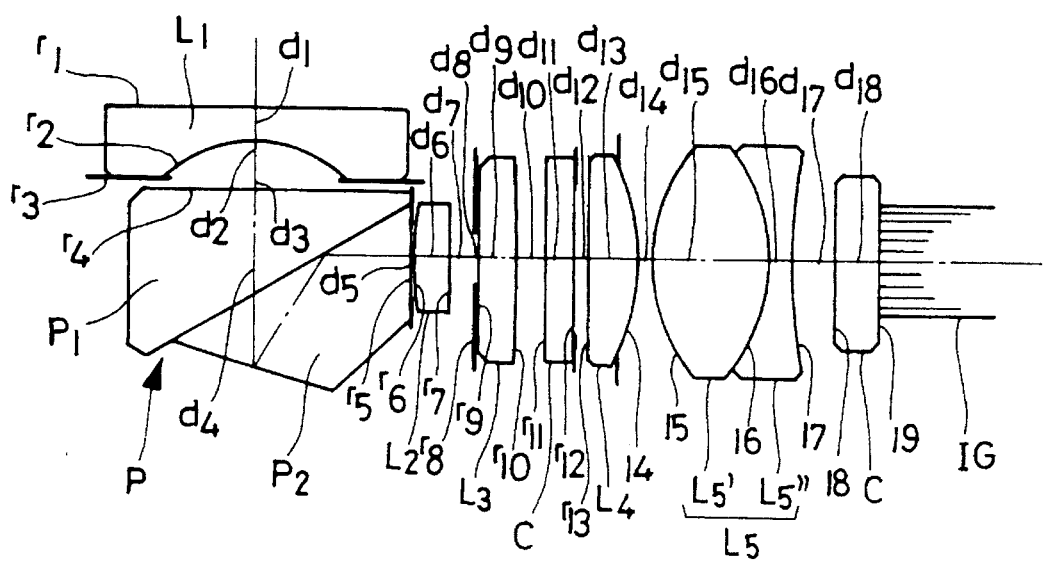

FIG. 17 and FIG. 18 show sectional views illustrating compositions of an objective optical system for endoscopes which is preferred as the fifth embodiment of the present invention. The objective optical system for endoscopes is equipped with a side viewing type leading end adaptor for observing an object located at a long distance in a condition shown in FIG. 17, whereas the objective optical system is equipped with a side viewing type leading end adaptor for observing an object located at a short distance in another condition shown in FIG. 18.

The objective lens system for endoscopes shown in FIG. 17 is a leading end adaptor type objective lens system comprising a leading end adaptor which is composed of a negative lens component $L_1$, a side viewing prism P consisting of two prisms $P_1$ and $P_2$ cemented to each other, a positive lens component $L_2$, an aperture stop and a focal point adjusting lens component $L_3$; and a cover glass plate C, a positive lens component $L_4$, a cemented lens component $L_5$ which consists of a positive lens element $L_5'$ and a negative lens element $L_5''$, a cover glass plate C and an image guide fiber bundle IG for leading an image to an eyepiece lens component which are disposed in the main body of an endoscope. In the objective lens system shown in FIG. 18, a focal point adjusting lens component $L_3'$ which has a convex surface $r_{10}$ on the object side is adopted in place of the focal point adjusting lens component $L_3$ used in the objective lens system shown in FIG. 17. Both the objective lens systems have a common field angle of 120°.

Figure 19:
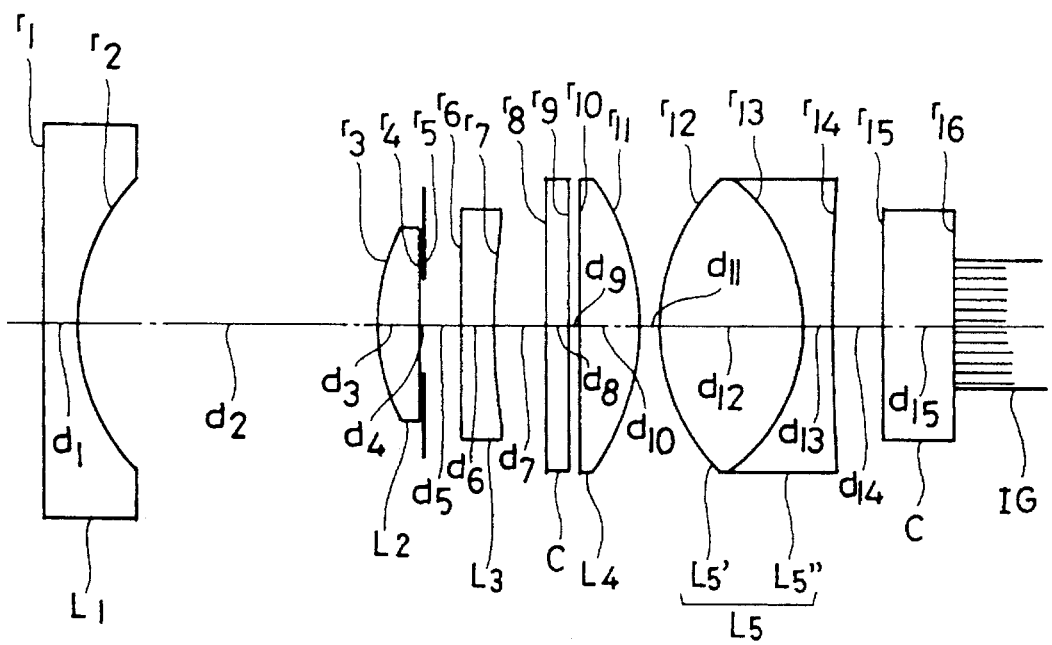
FIG. 19 and FIG. 20 show sectional views illustrating compositions of an objective optical system for endoscopes which is preferred as a sixth embodiment of the present invention.
Figure 20:
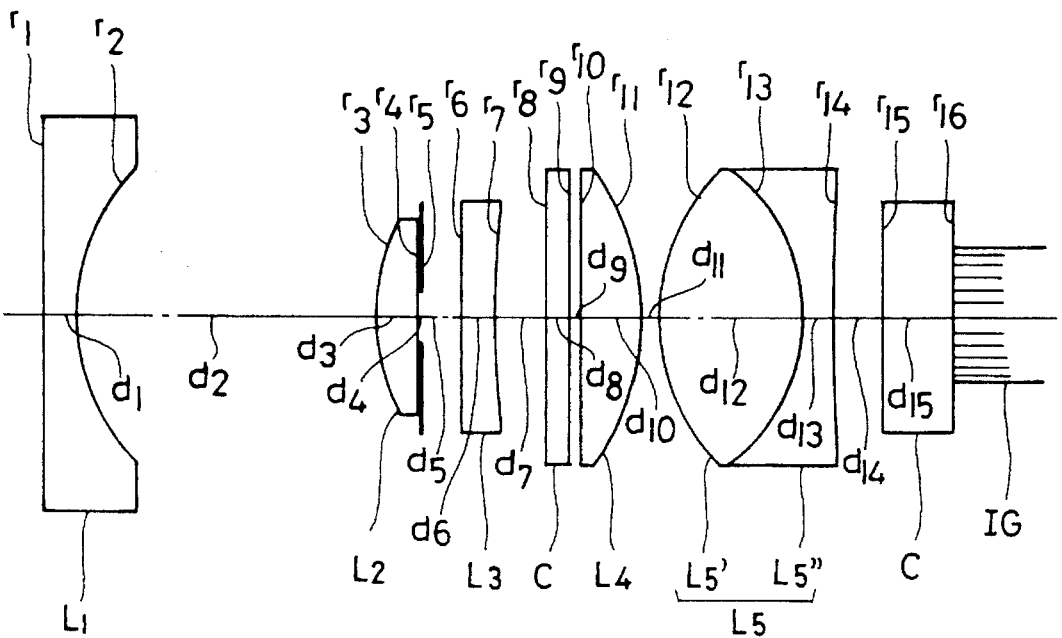

FIG. 19 and FIG. 20 show sectional views illustrating compositions of an objective optical system for endoscopes which is preferred as the sixth embodiment of the present invention. The objective lens system shown in FIG. 19 is equipped with a direct viewing type leading end adaptor for observing an object located at a long distance, whereas the objective lens system shown in FIG. 20 uses a direct viewing type leading end adaptor for observing an object located at a short distance. The objective lens system shown in FIG. 19 is a leading end adaptor type objective lens system comprising a leading end adaptor which consists, in order from the object side, of a negative lens component $L_1$, a positive lens component $L_2$, an aperture stop and a focal point adjusting lens component $L_3$; and a cover glass plate C, a positive lens component $L_4$, a cemented lens component $L_5$ consisting of a positive lens element $L_5'$ and a negative lens element $L_5''$, and a cover glass plate C which are disposed in the main body of an endoscope; an image guide fiber bundle IG for leading an image to an eyepiece lens component. Further, in the objective lens system shown in FIG. 20, a focal point adjusting lens component $L_3'$ which has an image side surface $r_7$ having curvature lower than that on an image side surface of the focal point adjusting lens component $L_3$ shown in FIG. 19 so that the objective optical system for endoscopes is focused on an object located at a short distance. These objective lens systems have a field angle of 90°.

Figure 21:
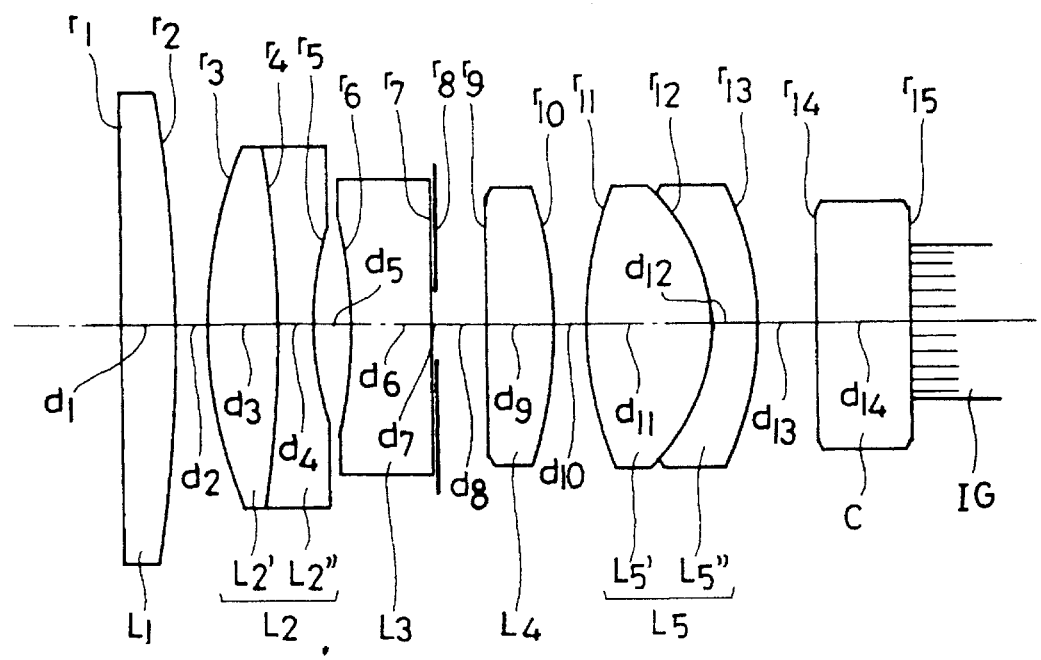
FIG. 21 and FIG. 22 show sectional view illustrating compositions of an objective optical system for endoscopes which is preferred as a seventh embodiment of the present invention.
Figure 22:
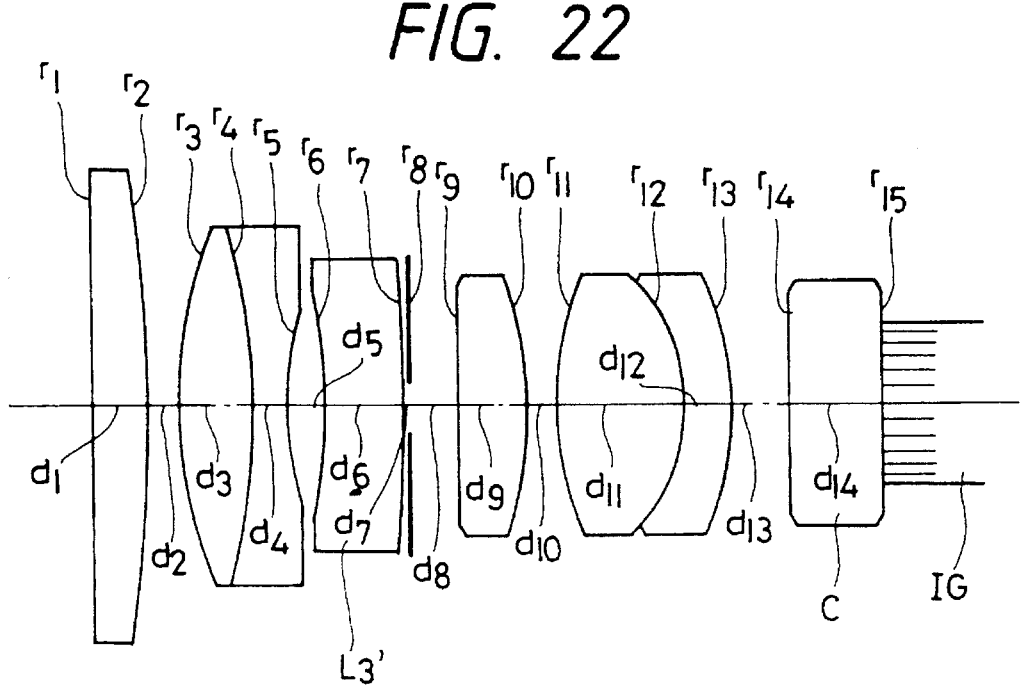
Figure 23:
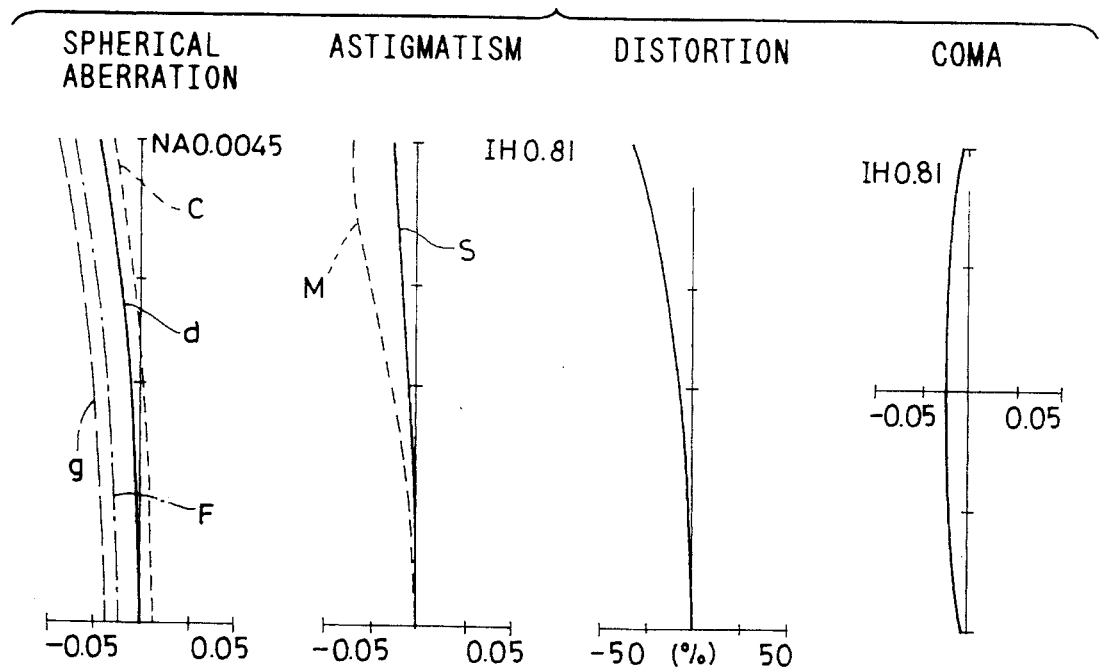
FIG. 23 and FIG. 24 show graphs illustrating aberration characteristics of the first embodiment of the objective optical system for endoscopes according to the present invention when the objective optical system is set for observing an object located at a long distance and at a short distance respectively.
Figure 24:
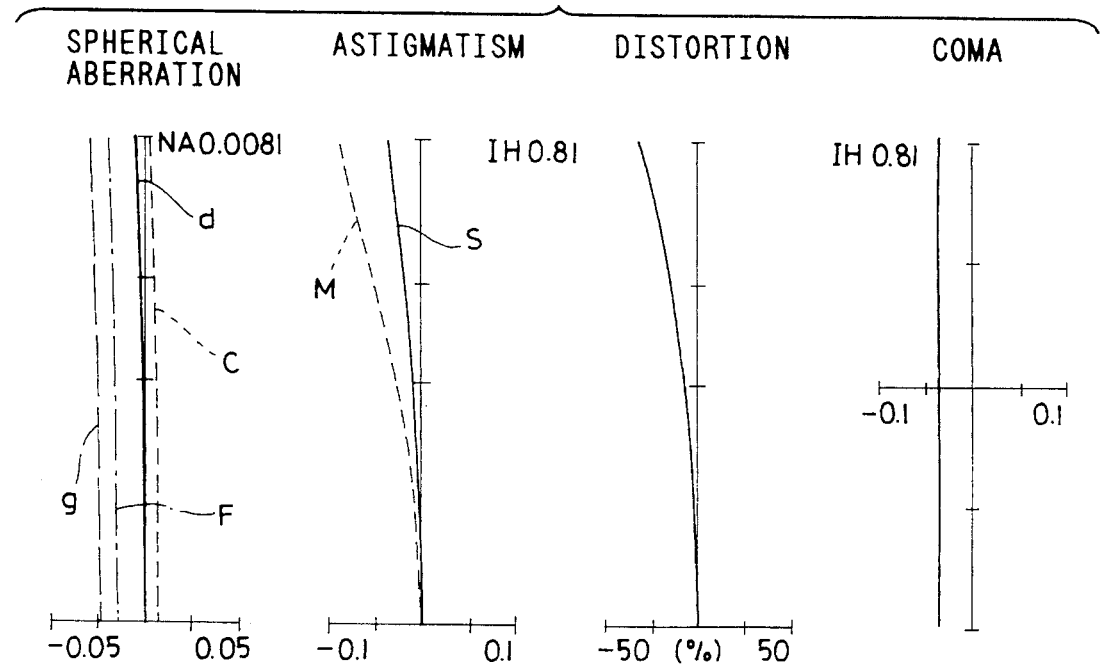
Figure 25:
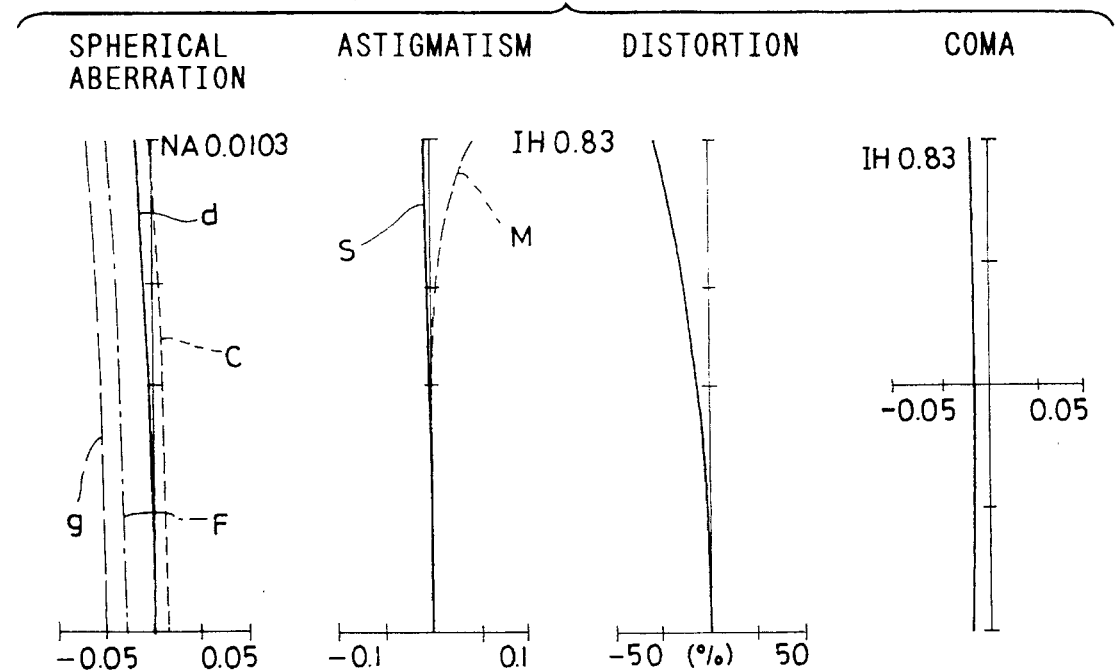
FIG. 25 and FIG. 26 show graphs illustrating aberration characteristics of the second embodiment of the objective optical system for endoscopes according to the present invention when it is set for observing an object located at a long distance and at a short distance respectively.
Figure 26:
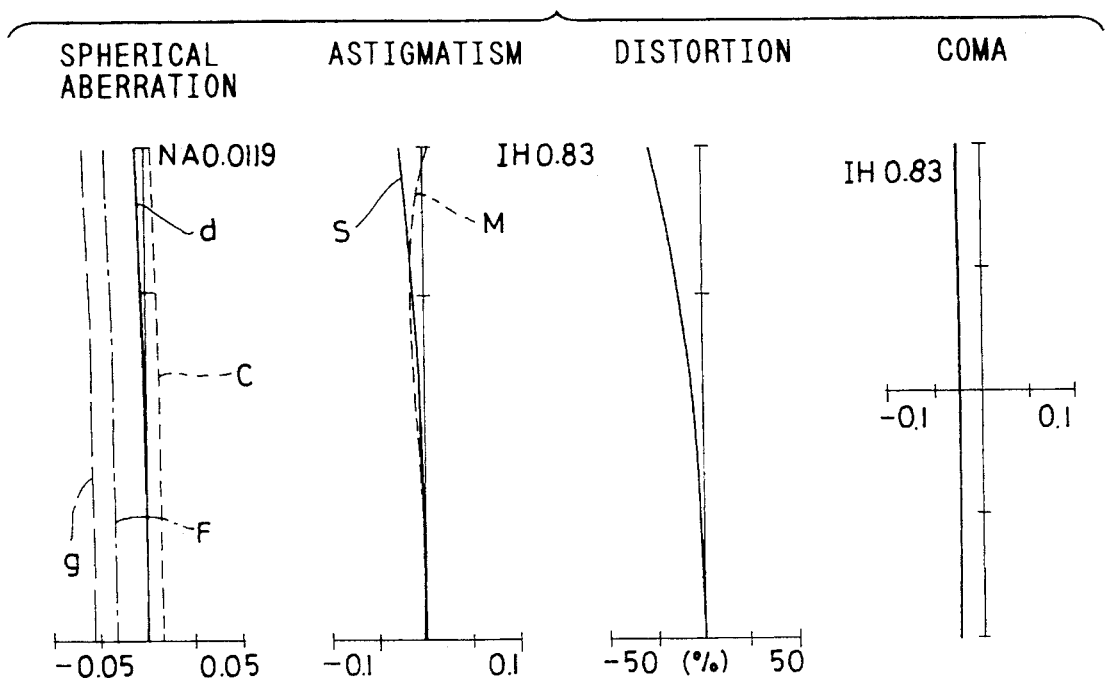
Figure 27:
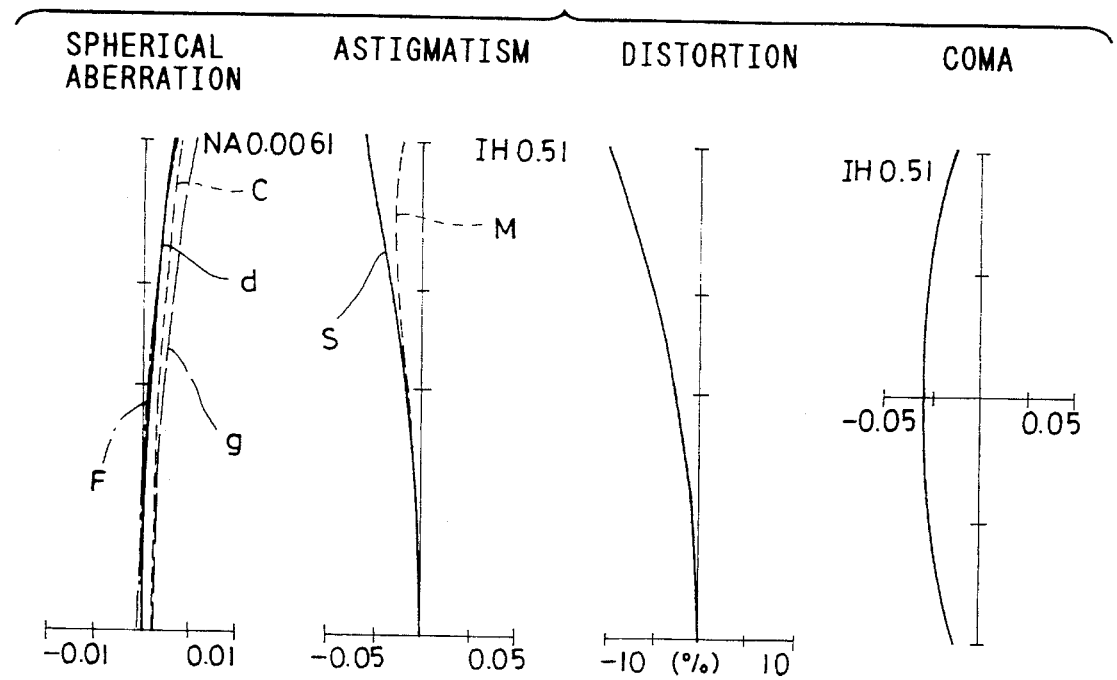
FIG. 27 and FIG. 28 show graphs illustrating aberration characteristics of the third embodiment of the objective optical system for endoscopes according to the present invention when it is set for observing an object located at a long distance and at a short distance respectively.
Figure 28:
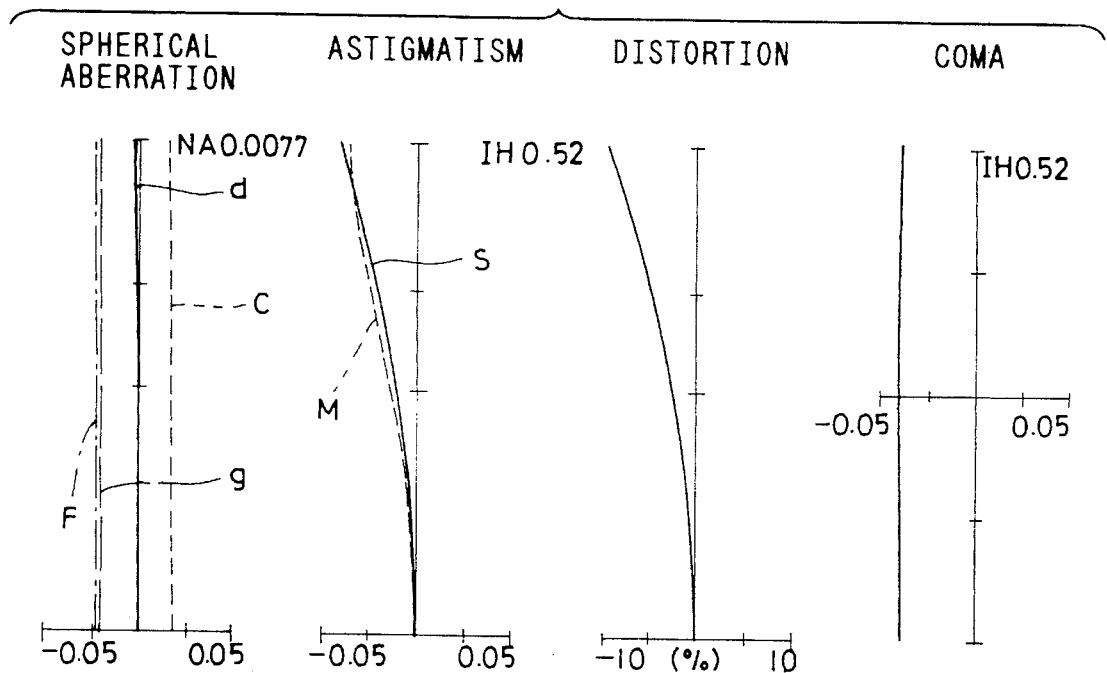
Figure 29:
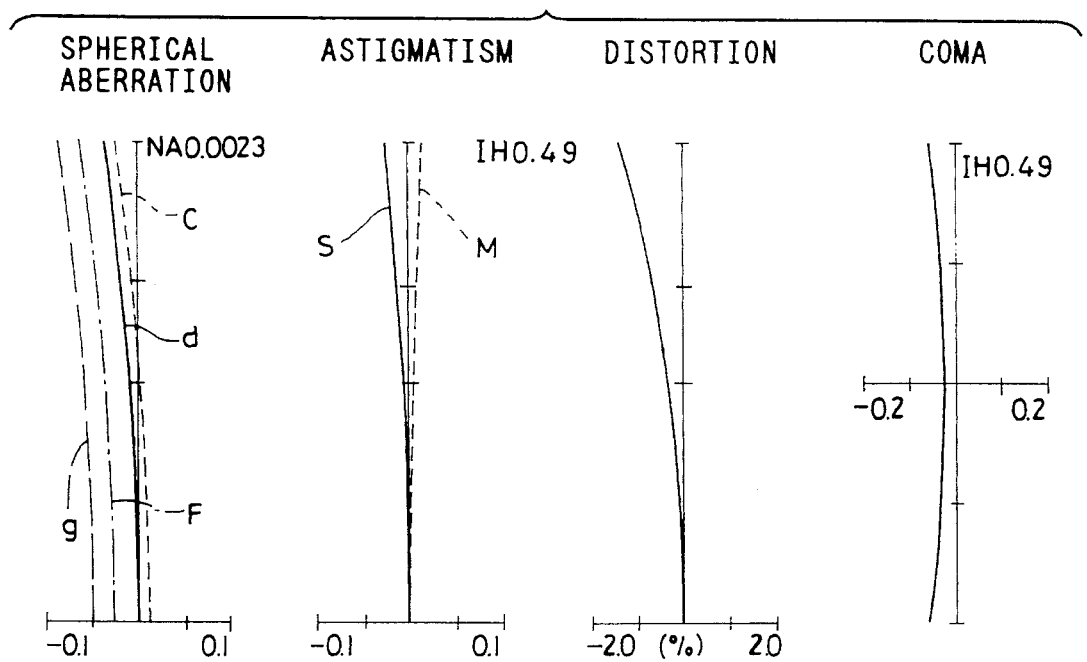
FIG. 29 and FIG. 30 show graphs illustrating aberration characteristics of the fourth embodiment of the objective optical system for endoscopes according to the present invention when it is set for observing an object located at a long distance and at a short distance respectively.
Figure 30:
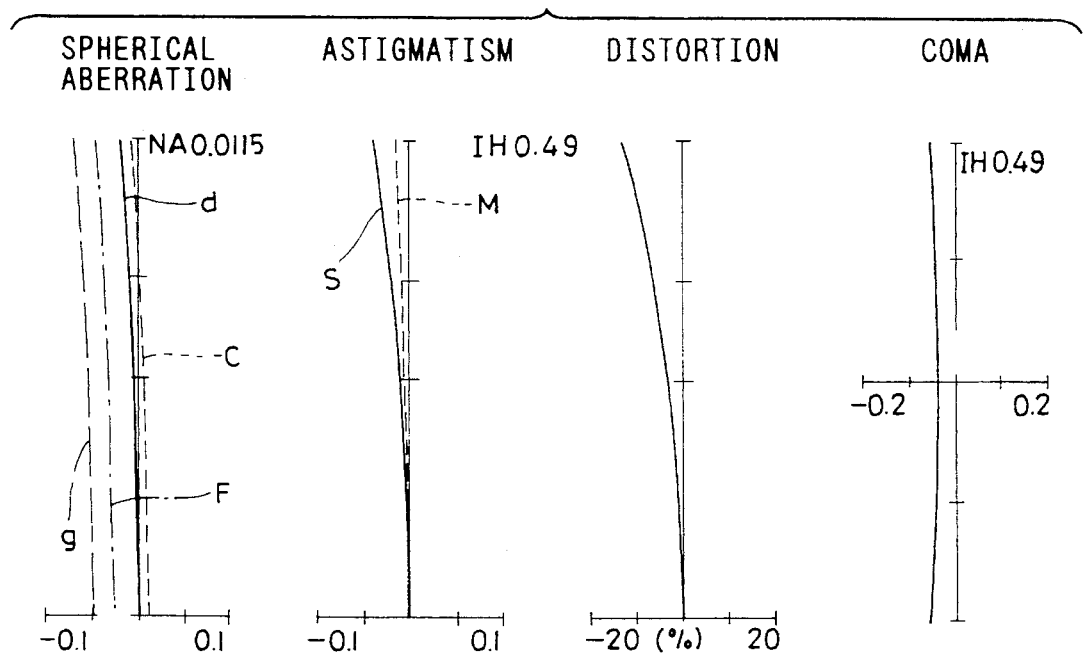
Figure 31:
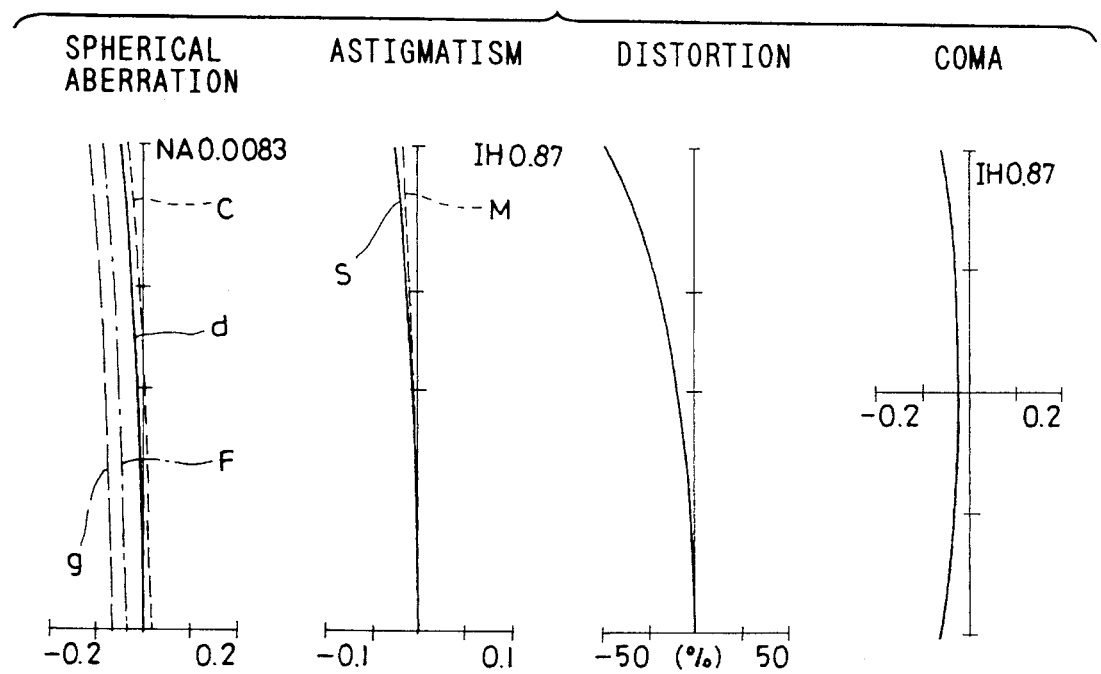
FIG. 31 and FIG. 32 show curves visualizing aberration characteristics of the fifth embodiment of the objective optical system for endoscopes according to the present invention when it is set for observing an object located at a long distance and at a short distance respectively.
Figure 32:
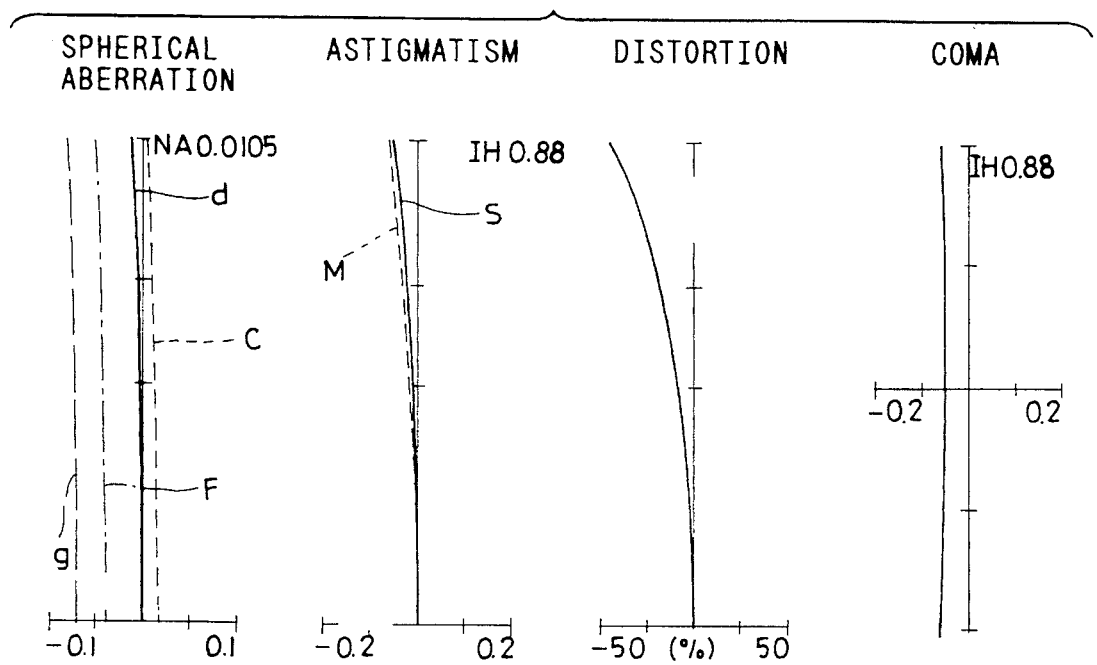
Figure 33:
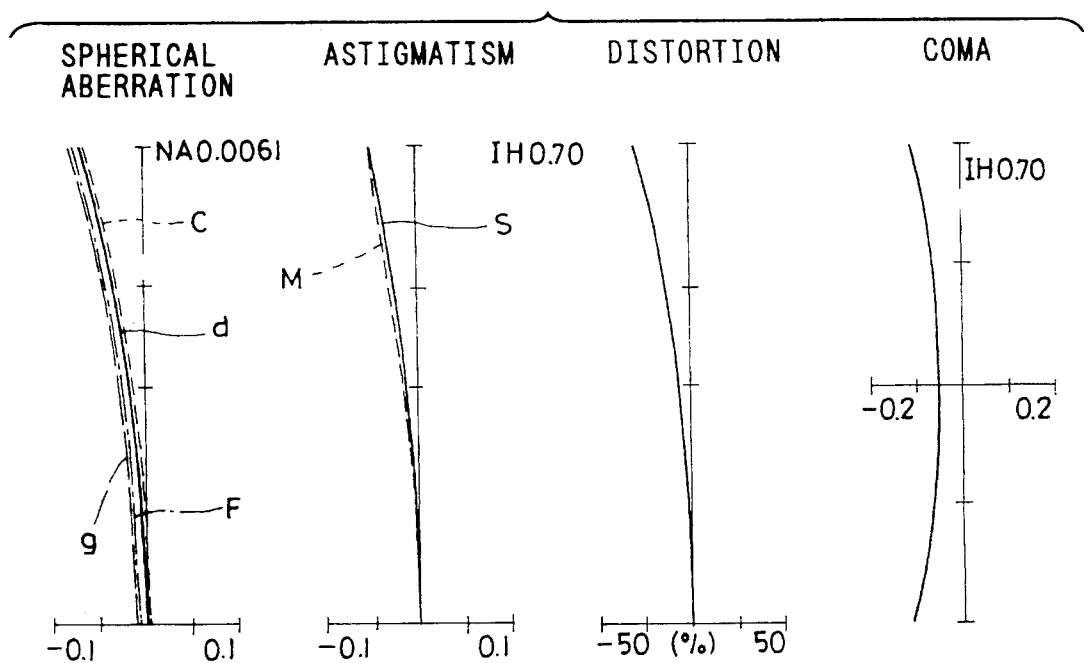
FIG. 33 and FIG. 34 show curves visualizing aberration characteristics of the sixth embodiment of the objective optical system for endoscopes according to the present invention when it is set for observing an object located at a long distance and at a short distance respectively.
Figure 34:
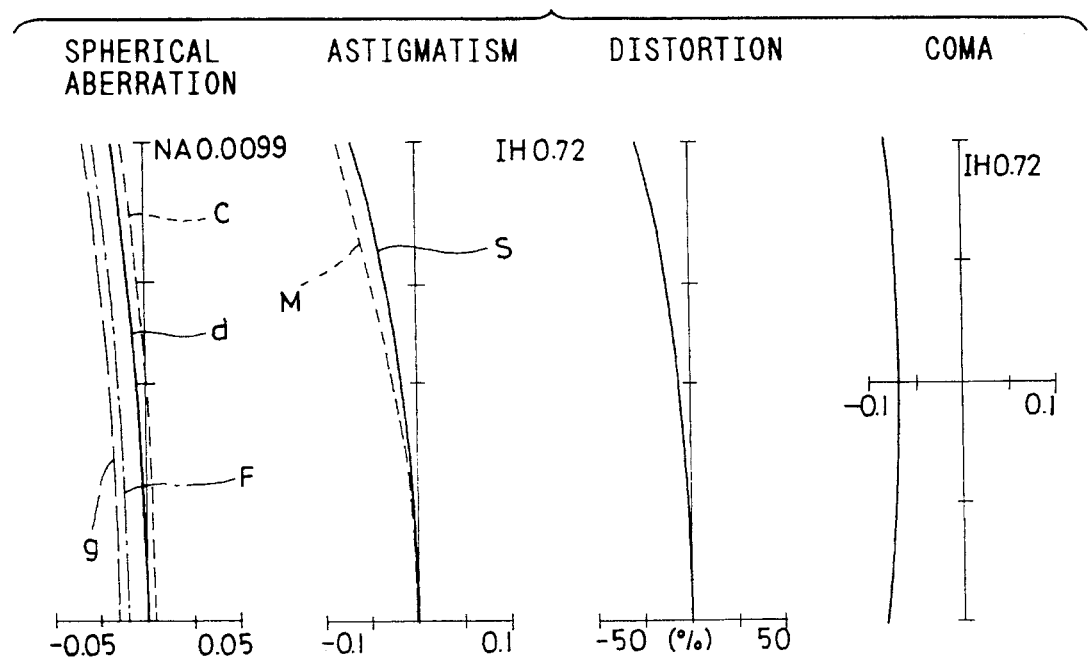
Figure 35:
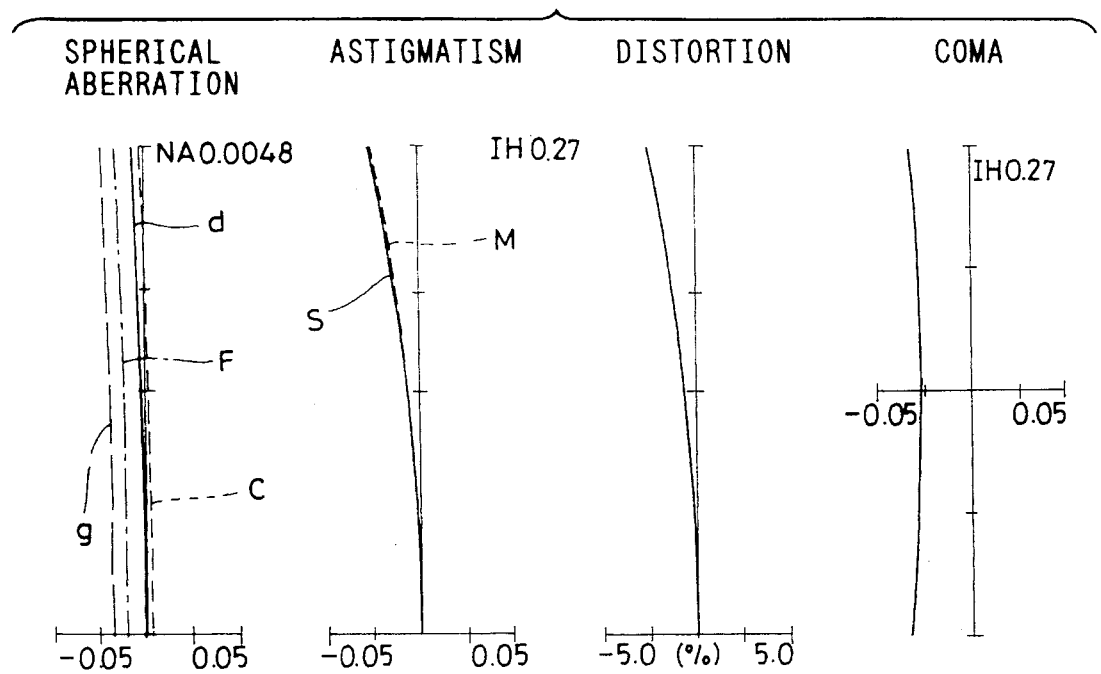
FIG. 35 and FIG. 36 shows curves visualizing aberration characteristics of the seventh embodiment of the objective optical system for endoscopes according to the present invention when it is set for observing an object located at a long distance and at a short distance respectively.
Figure 36:
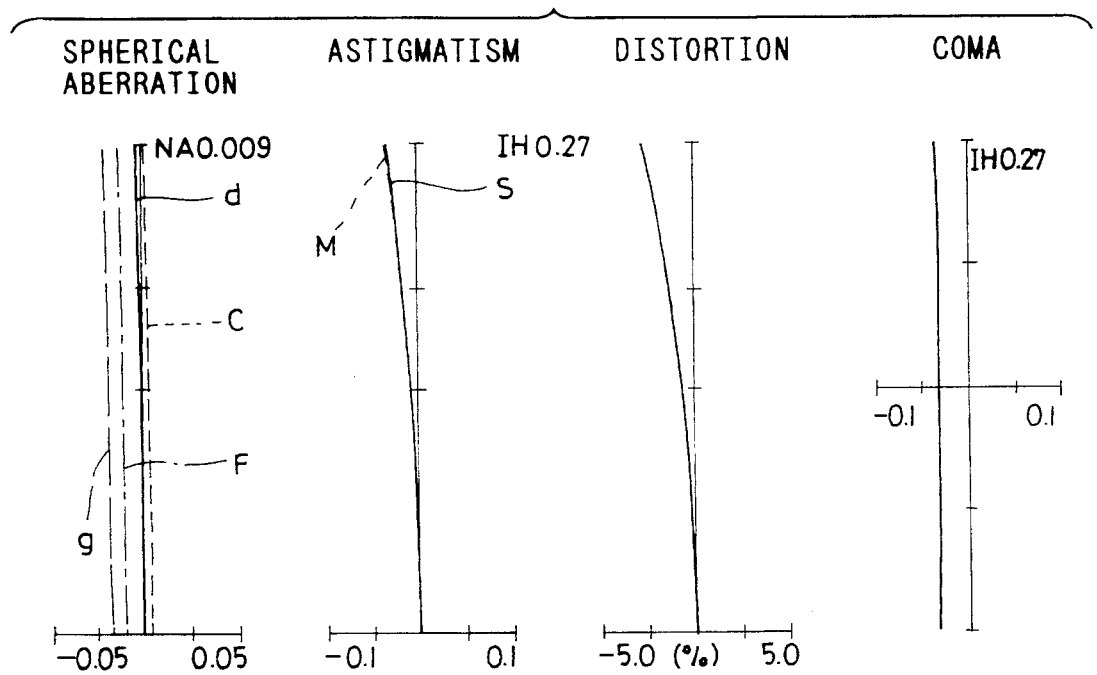

FIG. 21 and FIG. 22 show sectional views illustrating compositions of the seventh embodiment of the objective optical system for endoscopes according to the present invention. FIG. 21 shows the objective optical system in a condition where it is equipped with a direct viewing type adaptor for observing an object located at a long distance, whereas FIG. 22 shows the objective optical system in another condition where it is equipped with a direct viewing type adaptor for observing an object located at a short distance. The objective optical system shown in FIG. 21 is a leading end adaptor type objective optical system for endoscopes comprising: a leading end adaptor which consists, in order from the object side, of a positive lens component $L_1$, a cemented lens component $L_2$ consisting of a positive lens element $L_2'$ and a negative lens element $L_2''$, a focal point adjusting lens component $L_3$ and an aperture stop AS; a positive lens component $L_4$; a cemented lens component $L_5$ which consists of a positive lens element $L_5'$ and a negative lens element $L_5''$; a cover glass plate C; and an image guide fiber bundle IG. The objective optical system shown in FIG. 22 adopts a focal point adjusting lens component $L_3$, having a convex surface $r_2$ on the image side in place of the focal point adjusting lens component $L_3$ shown in FIG. 21 and an aperture stop which has a smaller diameter for increasing a depth of field. This objective optical system has a field angle of 30°. In addition, the aperture stops are disposed in the seventh embodiment at a location which is different from those selected for the first through sixth embodiments described above.

The fifth through seventh embodiments of the present invention have the numerical data which are listed below:

Embodiment 5 for observing object at long distance f=1.000, image height=0.8688, $f_B$=0.046, 2ω=119.486°, object distance=−22.2094

| | | |
|---|---|---|
| $r_1 = \infty$ | | |
| $d_1 = 0.5178$ | $n_1 = 1.88300$ | $v_1 = 40.78$ |
| $r_2 = 2.1197$ | | |

-continued

| | | |
|---|---|---|
| $d_2 = 0.6329$ | | |
| $r_3 = \infty$ | | |
| $d_3 = 0.1726$ | | |
| $r_4 = \infty$ | | |
| $d_4 = 6.3291$ | $n_2 = 1.88300$ | $v_2 = 40.78$ |
| $r_5 = \infty$ | | |
| $d_5 = 0.0575$ | | |
| $r_6 = 5.4833$ | | |
| $d_6 = 0.5754$ | $n_3 = 1.84666$ | $v_3 = 23.78$ |
| $r_7 = \infty$ | | |
| $d_7 = 0.4258$ | | |
| $r_8 = \infty$ (stop) | | |
| $d_8 = 0.0345$ | | |
| $r_9 = \infty$ | | |
| $d_9 = 0.4603$ | $n_4 = 1.51633$ | $v_4 = 64.15$ |
| $r_{10} = \infty$ | | |
| $d_{10} = 0.5984$ | | |
| $r_{11} = \infty$ | | |
| $d_{11} = 0.4603$ | $n_5 = 1.51633$ | $v_5 = 64.15$ |
| $r_{12} = \infty$ | | |
| $d_{12} = 0.2301$ | | |
| $r_{13} = \infty$ | | |
| $d_{13} = 0.8055$ | $n_6 = 1.51633$ | $v_6 = 64.15$ |
| $r_{14} = -3.6318$ | | |
| $d_{14} = 0.2647$ | | |
| $r_{15} = 2.8573$ | | |
| $d_{15} = 1.9102$ | $n_7 = 1.77250$ | $v_7 = 49.66$ |
| $r_{16} = -2.8573$ | | |
| $d_{16} = 0.4028$ | $n_8 = 1.78472$ | $v_8 = 25.68$ |
| $r_{17} = 9.0909$ | | |
| $d_{17} = 0.7020$ | | |
| $r_{18} = \infty$ | | |
| $d_{18} = 0.7250$ | $n_9 = 1.51633$ | $v_9 = 64.15$ |
| $r_{19} = \infty$ | | |
| $|\Delta f_{B6}/f_6^2| = 0.0006350306$ | | | for observing object at short distance f=1.000, image height=0.8830, $f_B$=0.026, 2ω120.688°, object distance=−7.6023

| | | |
|---|---|---|
| $r_1 = \infty$ | | |
| $d_1 = 0.5263$ | $n_1 = 1.88300$ | $v_1 = 40.78$ |
| $r_2 = 2.1544$ | | |
| $d_2 = 0.6433$ | | |
| $r_3 = \infty$ | | |
| $d_3 = 0.1754$ | | |
| $r_4 = \infty$ | | |
| $d_4 = 6.4327$ | $n_2 = 1.88300$ | $v_2 = 40.78$ |
| $r_5 = \infty$ | | |
| $d_5 = 0.0585$ | | |
| $r_6 = 5.5731$ | | |
| $d_6 = 0.5848$ | $n_3 = 1.84666$ | $v_3 = 23.78$ |
| $r_7 = \infty$ | | |
| $d_7 = 0.4327$ | | |
| $r_8 = \infty$ (stop) | | |
| $d_8 = 0.0351$ | | |
| $r_9 = \infty$ | | |
| $d_9 = 0.5848$ | $n_4 = 1.51633$ | $v_4 = 64.15$ |
| $r_{10} = -46.7626$ | | |
| $d_{10} = 0.4912$ | | |
| $r_{11} = \infty$ | | |
| $d_{11} = 0.4678$ | $n_5 = 1.51633$ | $v_5 = 64.15$ |
| $r_{12} = \infty$ | | |
| $d_{12} = 0.2339$ | | |
| $r_{13} = \infty$ | | |
| $d_{13} = 0.8187$ | $n_6 = 1.51633$ | $v_6 = 64.15$ |
| $r_{14} = -3.6912$ | | |
| $d_{14} = 0.2690$ | | |
| $r_{15} = 2.9041$ | | |
| $d_{15} = 1.9415$ | $n_7 = 1.77250$ | $v_7 = 49.66$ |
| $r_{16} = -2.9041$ | | |
| $d_{16} = 0.4094$ | $n_8 = 1.78472$ | $v_8 = 25.68$ |
| $r_{17} = 9.2398$ | | |
| $d_{17} = 0.7135$ | | |
| $r_{18} = \infty$ | | |
| $d_{18} = 0.7368$ | $n_9 = 1.51633$ | $v_9 = 64.15$ |
| $r_{19} = \infty$ | | |

$|\Delta f_{B6}/f_6^2| = 0.0020988779$
$|\{\sin^{-1}(h/f) - \sin^{-1}(h/f')\}/\sin^{-1}(h/f)| = 0.010059756$

Embodiment 6 for observing object at long distance
f=1.000, image height=0.7045, $f_B$= 0.046,
2ω=90.806°, object distance=−30.5400

| | | |
|---|---|---|
| $r_1 = \infty$ | | |
| $d_1 = 0.3724$ | $n_1 = 1.88300$ | $v_1 = 40.78$ |
| $r_2 = 2.1726$ | | |
| $d_2 = 3.2464$ | | |
| $r_3 = 2.2346$ | | |
| $d_3 = 0.4655$ | $n_2 = 1.51633$ | $v_2 = 64.15$ |
| $r_4 = \infty$ | | |
| $d_4 = 0.0186$ | | |
| $r_5 = \infty$ (stop) | | |
| $d_5 = 0.4221$ | | |
| $r_6 = \infty$ | | |
| $d_6 = 0.3724$ | $n_3 = 1.88300$ | $v_3 = 40.78$ |
| $r_7 = 8.7232$ | | |
| $d_7 = 0.5400$ | | |
| $r_8 = \infty$ | | |
| $d_8 = 0.2483$ | $n_4 = 1.51633$ | $v_4 = 64.15$ |
| $r_9 = \infty$ | | |
| $d_9 = 0.1241$ | | |
| $r_{10} = \infty$ | | |
| $d_{10} = 0.6518$ | $n_5 = 1.51633$ | $v_5 = 64.15$ |
| $r_{11} = -2.6071$ | | |
| $d_{11} = 0.2173$ | | |
| $r_{12} = 2.1837$ | | |
| $d_{12} = 1.5518$ | $n_6 = 1.72916$ | $v_6 = 54.68$ |
| $r_{13} = -1.9056$ | | |
| $d_{13} = 0.3228$ | $n_7 = 1.84666$ | $v_7 = 23.78$ |
| $r_{14} = 25.4836$ | | |
| $d_{14} = 0.5338$ | | |
| $r_{15} = \infty$ | | |
| $d_{15} = 0.7697$ | $n_8 = 1.51633$ | $v_8 = 64.15$ |
| $r_{16} = \infty$ | | |
| $|\Delta f_{B6}/f_6^2| = 0.0358112952$ | | | for observing object at short distance
f=1.000, image height=0.7184, $f_B$=0.016,
2ω=92.434°, object distance=−8.3464

| | | |
|---|---|---|
| $r_1 = \infty$ | | |
| $d_1 = 0.3797$ | $n_1 = 1.88300$ | $v_1 = 40.78$ |
| $r_2 = 2.2152$ | | |
| $d_2 = 3.3102$ | | |
| $r_3 = 2.2785$ | | |
| $d_3 = 0.4747$ | $n_2 = 1.51633$ | $v_2 = 64.15$ |
| $r_4 = \infty$ | | |
| $d_4 = 0.0190$ | | |
| $r_5 = \infty$ (stop) | | |
| $d_5 = 0.4304$ | | |
| $r_6 = \infty$ | | |
| $d_6 = 0.3797$ | $n_3 = 1.88300$ | $v_3 = 40.78$ |
| $r_7 = 11.1652$ | | |
| $d_7 = 0.5506$ | | |
| $r_8 = \infty$ | | |
| $d_8 = 0.2532$ | $n_4 = 1.51633$ | $v_4 = 64.15$ |
| $r_9 = \infty$ | | |
| $d_9 = 0.1266$ | | |
| $r_{10} = \infty$ | | |
| $d_{10} = 0.6646$ | $n_5 = 1.51633$ | $v_5 = 64.15$ |
| $r_{11} = -2.6582$ | | |
| $d_{11} = 0.2215$ | | |
| $r_{12} = 2.2266$ | | |
| $d_{12} = 1.5823$ | $n_6 = 1.72916$ | $v_6 = 54.68$ |
| $r_{13} = -1.9430$ | | |
| $d_{13} = 0.3291$ | $n_7 = 1.84666$ | $v_7 = 23.78$ |
| $r_{14} = 25.9835$ | | |

| | | |
|---|---|---|
| $d_{14} = 0.5443$ | | |
| $r_{15} = \infty$ | | |
| $d_{15} = 0.7848$ | $n_8 = 1.51633$ | $v_8 = 64.15$ |
| $r_{16} = \infty$ | | |
| $|\Delta f_{B6}/f_6^2| = 0.0305184478$ | | |
| $|\{\sin^{-1}(h/f) - \sin^{-1}(h/f')\}/\sin^{-1}(h/f)| = 0.0179283307$ | | |

Embodiment 7 for observing object at long distance
f=1.000, image height=0.2657, $f_B$=0.010,
2ω=30.10°, object distance=−28.9013

| | | |
|---|---|---|
| $r_1 = \infty$ | | |
| $d_1 = 0.2000$ | $n_1 = 1.88300$ | $v_1 = 40.78$ |
| $r_2 = -4.9310$ | | |
| $d_2 = 0.1143$ | | |
| $r_3 = 1.6052$ | | |
| $d_3 = 0.2685$ | $n_2 = 1.72000$ | $v_2 = 43.70$ |
| $r_4 = -3.5196$ | | |
| $d_4 = 0.1214$ | $n_3 = 1.51633$ | $v_3 = 64.15$ |
| $r_5 = 1.1709$ | | |
| $d_5 = 0.1429$ | | |
| $r_6 = -1.4803$ | | |
| $d_6 = 0.2857$ | $n_4 = 1.51633$ | $v_4 = 64.15$ |
| $r_7 = \infty$ | | |
| $d_7 = 0.0171$ | | |
| $r_8 = \infty$ (stop) | | |
| $d_8 = 0.1829$ | | |
| $r_9 = \infty$ | | |
| $d_9 = 0.2457$ | $n_5 = 1.88300$ | $v_5 = 40.78$ |
| $r_{10} = -1.4469$ | | |
| $d_{10} = 0.1143$ | | |
| $r_{11} = 1.2177$ | | |
| $d_{11} = 0.4571$ | $n_6 = 1.60311$ | $v_6 = 60.70$ |
| $r_{12} = -0.6320$ | | |
| $d_{12} = 0.1714$ | $n_7 = 1.84666$ | $v_7 = 23.78$ |
| $r_{13} = -1.0526$ | | |
| $d_{13} = 0.2057$ | | |
| $r_{14} = \infty$ | | |
| $d_{14} = 0.3429$ | $n_8 = 1.51633$ | $v_8 = 64.15$ |
| $r_{15} = \infty$ | | |
| $|\Delta f_{B6}/f_6^2| = 0.0145309178$ | | | for observing object at short distance
f=1.000, image height=0.2722, $f_B$= 0.010,
2ω=30.10°, object distance=−9.3677

| | | |
|---|---|---|
| $r_1 = \infty$ | | |
| $d_1 = 0.2049$ | $n_1 = 1.88300$ | $v_1 = 40.78$ |
| $r_2 = -5.8920$ | | |
| $d_2 = 0.1171$ | | |
| $r_3 = 1.6246$ | | |
| $d_3 = 0.2804$ | $n_2 = 1.72000$ | $v_2 = 43.70$ |
| $r_4 = -2.4772$ | | |
| $d_4 = 0.1244$ | $n_3 = 1.51633$ | $v_3 = 64.15$ |
| $r_5 = 1.1555$ | | |
| $d_5 = 0.1464$ | | |
| $r_6 = -1.7339$ | | |
| $d_6 = 0.2927$ | $n_4 = 1.51633$ | $v_4 = 64.15$ |
| $r_7 = -6.7785$ | | |
| $d_7 = 0.0176$ | | |
| $r_8 = \infty$ (stop) | | |
| $d_8 = 0.1874$ | | |
| $r_9 = \infty$ | | |
| $d_9 = 0.2518$ | $n_5 = 1.88300$ | $v_5 = 40.78$ |
| $r_{10} = -1.4824$ | | |
| $d_{10} = 0.1171$ | | |
| $r_{11} = 1.2477$ | | |
| $d_{11} = 0.4684$ | $n_6 = 1.60311$ | $v_6 = 60.70$ |
| $r_{12} = -0.6475$ | | |
| $d_{12} = 0.1756$ | $n_7 = 1.84666$ | $v_7 = 23.78$ |
| $r_{13} = -1.0785$ | | |

-continued $d_{13} = 0.2108$
$r_{14} = \infty$
$\quad d_{14} = 0.3513 \quad n_8 = 1.51633 \quad v_8 = 64.15$
$r_{15} = \infty$
$|\Delta f_{B6}/f_6{}^2| = 0.013853912$
$|\{\sin^{-1}(h/f) - \sin^{-1}(h/f')\}/\sin^{-1}(h/f)| = 0$ In the first through seventh embodiments of the present invention which have been described above, the objective lens systems for observing the objects located at the long distances are fundamentally the same as the objective lens systems for observing the objects located at the short distances, except for the focal point adjusting lens components $L_3$ and $L_3'$ which are different from one another. However, the numerical data of these objective lens systems other than those of the focal point adjusting lens components are different from one another when the numerical data are normalized to focal lengths of the objective lens systems as wholes since the objective lens systems for observing the objects located at the long distances have focal lengths which are slightly different from those of the objective lens systems for observing the objects located at the short distances. As a result, the numerical data of the objective optical systems for endoscopes, except for those of the focal point adjusting lens components, are different from one another though the numerical data are actually the same as one another.

Though the leading end adaptor type objective optical systems for endoscopes have been preferred as the first through seventh embodiments described above, the present invention is applicable also to the adaptor type objective optical systems for endoscopes. Speaking concretely, it is possible to exchange only the focal point adjusting lens component and the aperture stop with others though the focal point adjusting lens component and the lens system disposed before the aperture stop are configured as an integral unit which is attachable and detachable to and from the main body of an endoscope in each of the embodiments described above.

In particular cases where endoscopes are to be used for observing locations under influences due to radiations, for example, interiors of nuclear reactors, it is necessary to take the following points into consideration. When energy of a radiation such as X-ray or gamma-ray drives out electrons from any kinds of ions composing glass materials, the electrons are accommodated into lattice defects in a glass structure which have positive electric charges suited for capturing the electrons, mainly cavities of oxygen ions, thereby producing characteristic absorption corresponding to the F center which appears in crystals of rock salt or the like. In cases of glass materials, locations for coupling with oxygen ions are of several types dependently on specific properties of internal structures of the glass materials and absorption due to continuous deviation caused by irregularities of atomic arrangement is overlapped with the characteristic absorption, whereby it is general that clear independent absorption is scarecely produced, but continuous absorption curves are formed. As a result, the glass materials are colored in brown, pink, etc., and exhibit remarkably lowered transmittance, thereby making it impossible to observe objects through the objective optical systems for endoscopes.

As glass materials which have radiation-resistant characteristics or which are not colored by radiations, there are known those which are prepared by adding cerium oxide to glass materials containing lead or barium at high ratios. However, the glass materials containing cerium are yellowish before irradiation with radiations due to absorption of rays having short wavelengths within the visible region under presence of $Ce^{4+}$. Heavy flint glass materials which have high refractive indices exhibit this tendency more remarkably and are strongly yellowish. Accordingly, images are strongly yellowish and favorable observations of these images are impossible when the objective optical systems for endoscopes are made of glass materials which contain cerium oxide at high ratios or have high refractive indices or when the optical systems have long optical paths.

FIG. 39 through FIG. 44 illustrate spectroscopic transmittance of radiation-resistant glass materials (10 mm thick) containing cerium oxide which are mentioned as items (1) through (6) below:

(1) Cerium oxide added to BK7 nd: 1.51630 vd: 64.36
(2) Cerium oxide added to SK nd: 1.61222 vd: 58.14
(3) Cerium oxide added to F2 nd: 1.62004 vd: 36.38
(4) Cerium oxide added to LAK9 nd: 1.69089 vd: 54.83
(5) Cerium oxide added to SF1 nd: 1.71414 vd: 29.72
(6) Cerium oxide added to Fn3 nd: 1.84738 vd: 23.86

As is seen from FIG. 39 to FIG. 44, glass materials which have higher refractive indics exhibit lower transmittance at the short wavelengths and are yellowish more remarkably. When objective optical systems for endoscopes are to be used for observing objects under influences due to radiations, it is necessary to manufacture objective lens systems by selecting radiation-resistant glass materials which has high refractive indices and configuring lens components so as to be thin for preventing images observed through the objective lens systems from being discolored.

The radiation-resistant glass materials containing cerium oxide which are listed as items (1) through (6) above exhibit transmittance listed below at 450 nm and 500 nm:
(Before irradiation with a radiation)

|     | 450 nm | 500 nm |
| --- | --- | --- |
| (1) | 90% | 91% |
| (2) | 84% | 88% |
| (3) | 85% | 89% |
| (4) | 78% | 85% |
| (5) | 52% | 81% |
| (6) | 2%  | 52% |

(A: Immediately after irradiation with a radiation B: Five days after irradiation with a radiation)

|     | 450 nm | | 500 nm | |
| --- | --- | --- | --- | --- |
| (1) | A 75% | B 77% | A 84% | B 85% |
| (2) | A 60% | B 65% | A 75% | B 80% |
| (3) | A 69% | B 73% | A 82% | B 85% |
| (4) | A 32% | B 36% | A 68% | B 73% |
| (5) | A 15% | B 21% | A 64% | B 70% |
| (6) | A  0% | B  0% | A 27% | B 33% |

As is understood from the tables shown above, these radiation-resistant glass materials do not allow remarkable lowering of transmittance thereof though allows slight lowering of transmittance at the shorter wavelength after irradiation with a radiation. Further, the transmittance of these glass materials is a little improve with lapse of time as is seen from the table listing transmittance values five days after the irradiation with the radiation.

An embodiment of the objective optical system for endoscopes according to the present invention which is configured so as to take the point described above into consideration will be described below:

Embodiment 8 f=1.019, F/4.245, image height=0.4984,
$f_B$=0.057, object distance=−9.4307

| | | | |
|---|---|---|---|
| $r_1 = \infty$ | | | |
| | $d_1 = 0.4205$ | $n_1 = 1.84738$ | $\nu_1 = 23.86$ |
| $r_2 = 0.9715$ | | | |
| | $d_2 = 0.5698$ | | |
| $r_3 = 1.4310$ | | | |
| | $d_3 = 0.8199$ | $n_2 = 1.84738$ | $\nu_2 = 23.86$ |
| $r_4 = \infty$ | | | |
| | $d_4 = 0.5359$ | | |
| $r_5 = \infty$ (stop) | | | |
| | $d_5 = 0.0000$ | | |
| $r_6 = 6.1696$ | | | |
| | $d_6 = 0.5205$ | $n_3 = 1.51630$ | $\nu_3 = 64.46$ |
| $r_7 = \infty$ | | | |
| | $d_7 = 0.3108$ | | |
| $r_8 = \infty$ | | | |
| | $d_8 = 0.4707$ | $n_4 = 1.84738$ | $\nu_4 = 23.86$ |
| $r_9 = -4.7539$ | | | |
| | $d_9 = 0.1973$ | | |
| $r_{10} = 1.7755$ | | | |
| | $d_{10} = 0.8298$ | $n_5 = 1.61222$ | $\nu_5 = 58.14$ |
| $r_{11} = -0.8794$ | | | |
| | $d_{11} = 0.3176$ | $n_6 = 1.84738$ | $\nu_6 = 23.86$ |
| $r_{12} = -1.6511$ | | | |
| | $d_{12} = 0.3899$ | | |
| $r_{13} = \infty$ | | | |
| | $d_{13} = 0.6431$ | $n_7 = 1.51630$ | $\nu_7 = 64.46$ |
| $r_{14} = \infty$ | | | |

Figure 37:
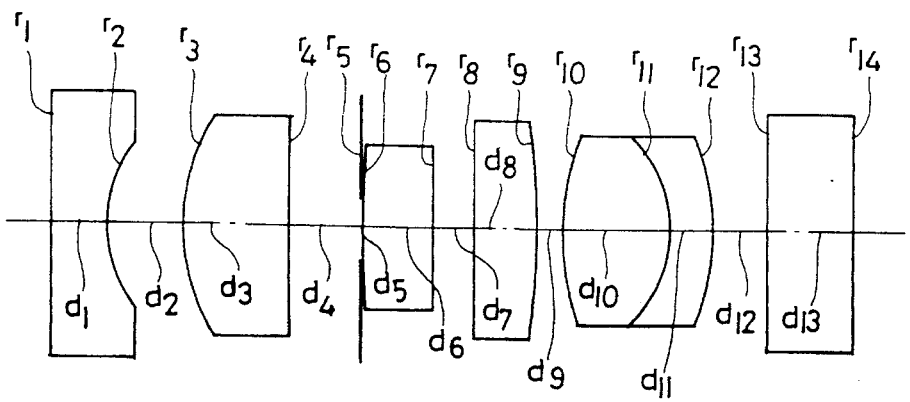
FIG. 37 shows a sectional view illustrating a composition of an eighth embodiment of the objective optical system for endoscopes according to the present invention.
Figure 38:
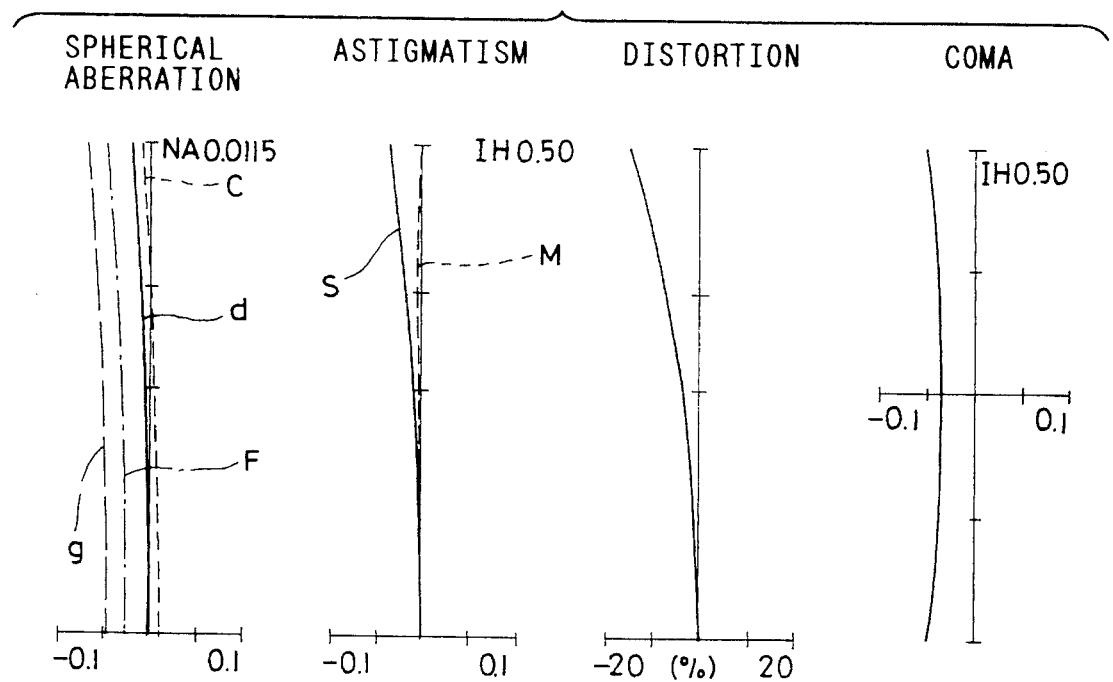
FIG. 38 show graphs illustrating aberration characteristics of the eighth embodiment of the objective optical system for endoscopes according to the present invention.
Figure 39:
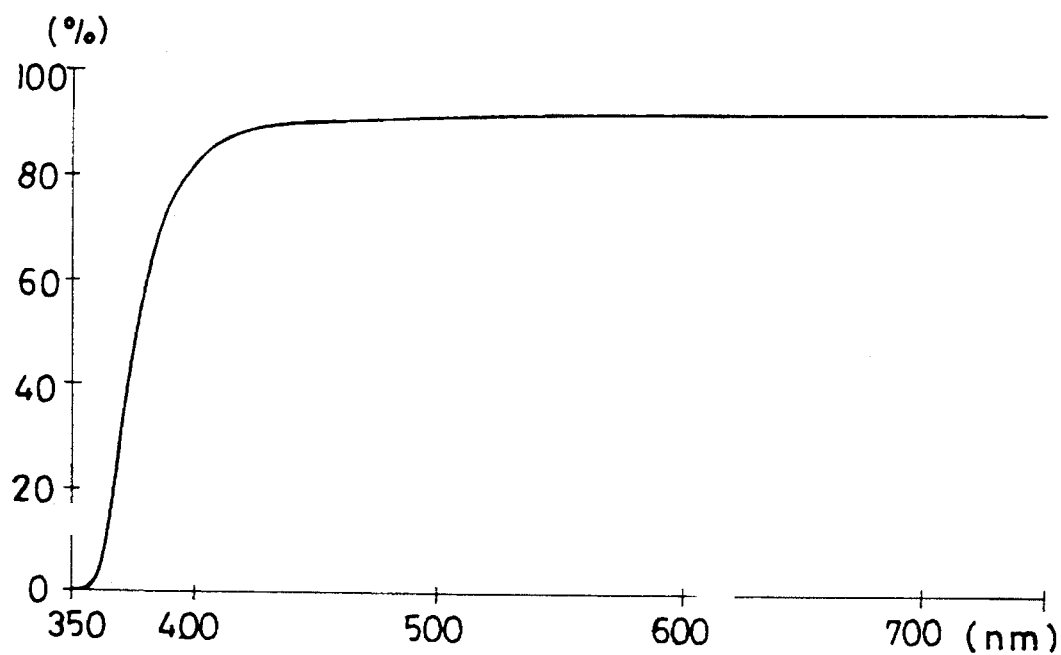
FIG. 39 through FIG. 44 show graphs illustrating spectroscopic transmittance characteristics of radiation-resistant glass materials.
Figure 40:
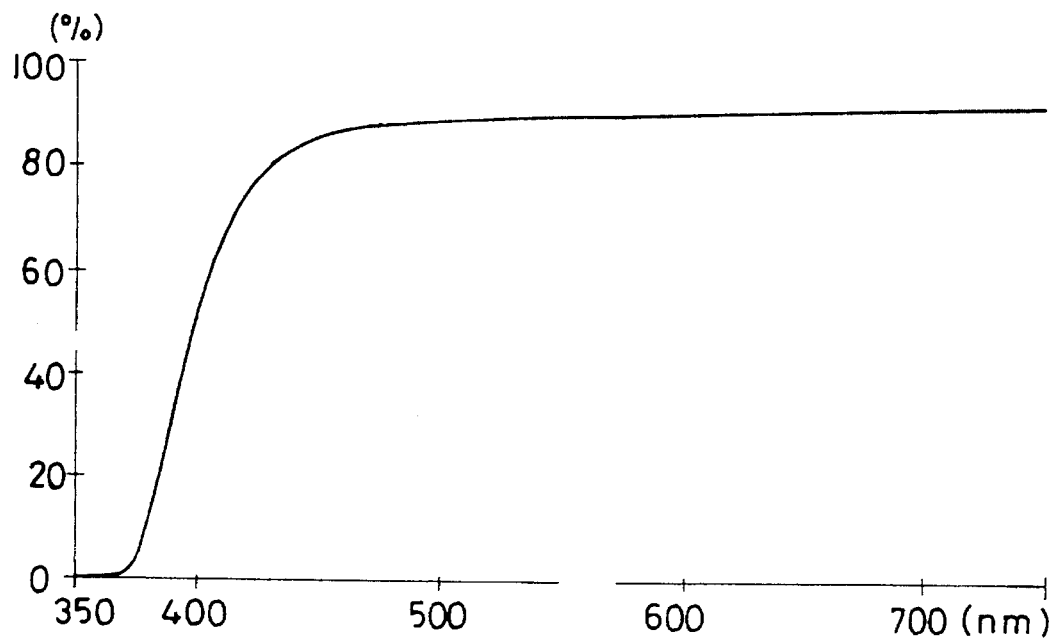
Figure 41:
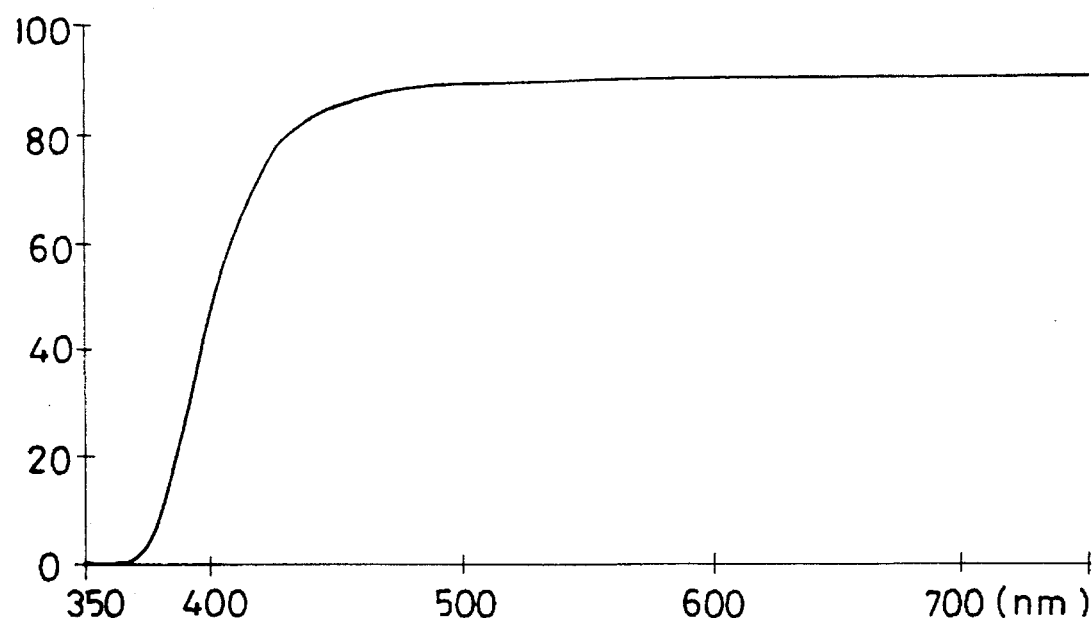
Figure 42:
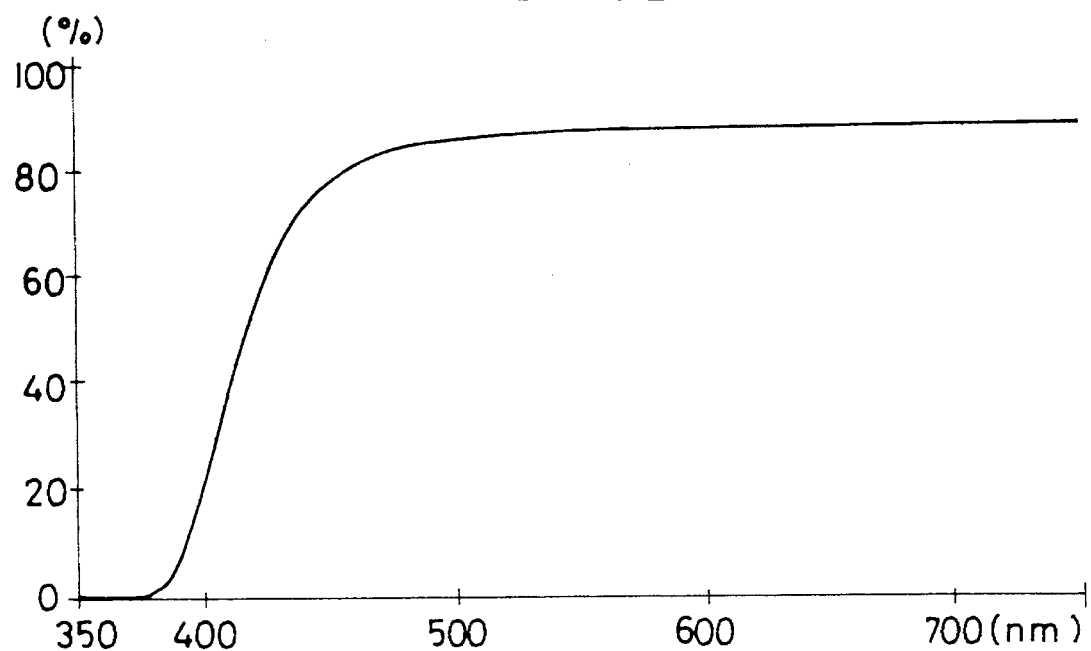
Figure 43:
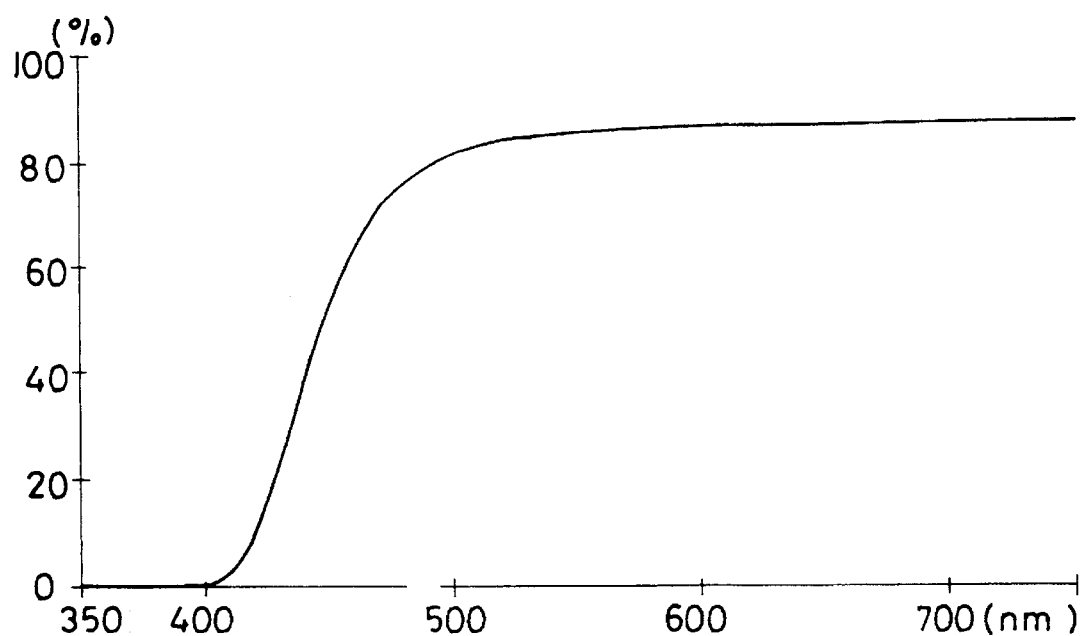
Figure 44:
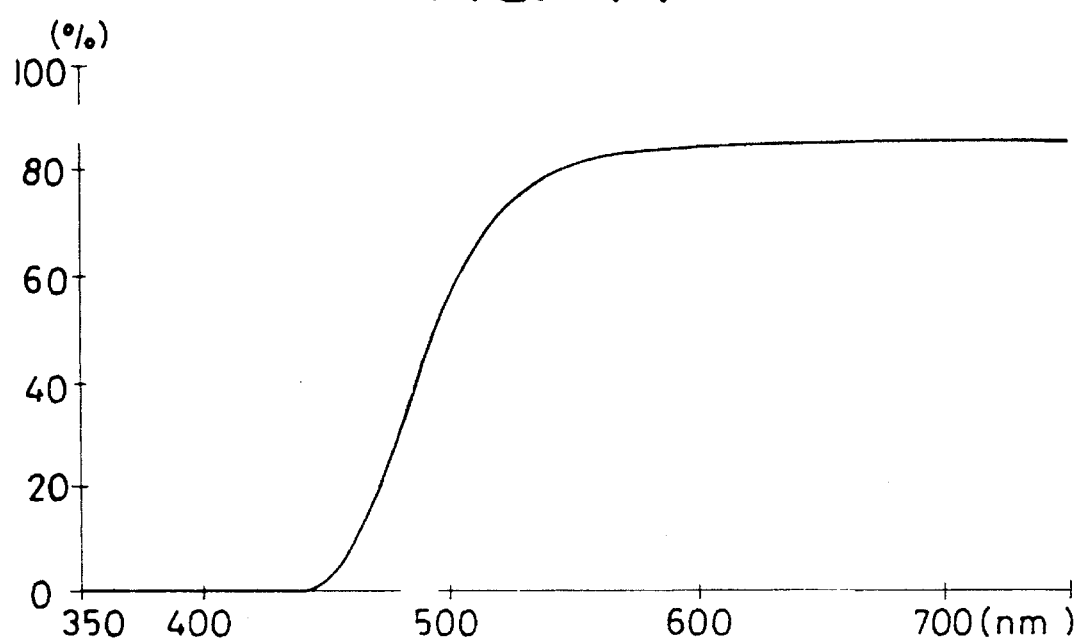

The eighth embodiment of the objective optical system for endoscopes according to the present invention is a direct viewing type objective optical system which has the composition shown in FIG. 37 and is configured for observing an object located at a long distance. The eighth embodiment permits observing an object located at a short distance when an aperture stop and a lens component disposed immediately after this aperture stop are exchanged with others.

In each of the first through eighth embodiments of the present invention described above, the focal point adjusting lens component may be omitted when a plane parallel plate is adopted as this lens component.

The objective optical system for endoscopes according to the present invention permits adjusting a distance to an object to be observed simply by exchanging a lens component disposed in the vicinity of an aperture stop with another lens component. Further, the objective optical system for endoscopes according to the present invention permits selecting an optimum depth of field simply by changing a diameter of the aperture stop along with the exchange of the lens component.

We claim:

1. An endoscope comprising:
an endoscope body;
a master lens unit which is fixed to a distal end of said endoscope body for forming an image of an object; and
a plurality of adaptor units each of which comprises lens components disposed on one optical axis and an aperture stop such that said adaptor units have focal lengths different from one another;
wherein said adaptor units are attachable and detachable to and from said distal end of said endoscope body,
wherein a first objective optical system defined by lens components from a first adapter unit from said plurality of adaptor units and said master lens unit if said first adaptor unit is attached to an object side of said master lens unit,
wherein a focal length of said first objective optical system equipped with said first adaptor unit is different from a focal length of a second objective optical system equipped with a second adaptor unit, and
wherein the lens component which is disposed in the vicinity of said aperture stop of said first adaptor unit may selectively vary from the lens component which is disposed in the vicinity of said second adaptor unit.

2. An endoscope according to claim 1, wherein said aperture stop is disposed on the object side and proximate to a first lens component of said first adaptor unit, wherein the first lens component is the component closest to said master lens unit; and
wherein the focal length of said first adaptor lens component is selectively varied from a second lens component which is the closet second adaptor lens component to said master lens unit.

3. An endoscope according to claim 2, wherein an objective optical lens system comprised of said master lens unit and said adaptor unit attached to said master lens unit is defined as a first objective optical lens system and the other objective optical lens system consisting of said master lens unit and said second adaptor unit attached to said master lens unit is defined as a second objective optical lens system, said first objective optical system and said second objective optical system have substantially the same field angle but different observation distance.

4. An endoscope according to claim 2, wherein aperture diameters of said aperture stops of said plurality of adaptor units are different in accordance with said focal length of said rearmost lens component.

5. An endoscope according to claim 2, wherein said plurality of adaptor units includes adaptor units whose angle of fields are different from one another and adaptor units whose viewing directions are different from one another.

6. An endoscope according to claim 2, wherein said master lens unit has no focusing function and each of said lens components is always fixed on said optical axis.

* * * * *